US012064196B2

(12) United States Patent
Lee et al.

(10) Patent No.: US 12,064,196 B2
(45) Date of Patent: Aug. 20, 2024

(54) MASTER CONTROL SYSTEMS FOR ROBOTIC SURGICAL SYSTEMS

(71) Applicant: EndoQuest Robotics, Inc., Houston, TX (US)

(72) Inventors: Seoungkyou Lee, Houston, TX (US); Jiwon Choi, Houston, TX (US); Yongman Park, Houston, TX (US); Jeihan Lee, Houston, TX (US); Dongsuk Shin, Houston, TX (US)

(73) Assignee: EndoQuest Robotics, Inc., Houston, TX (US)

( * ) Notice: Subject to any disclaimer, the term of this patent is extended or adjusted under 35 U.S.C. 154(b) by 0 days.

(21) Appl. No.: 18/121,983

(22) Filed: Mar. 15, 2023

(65) Prior Publication Data

US 2023/0285090 A1    Sep. 14, 2023

Related U.S. Application Data

(63) Continuation of application No. PCT/US2022/051217, filed on Nov. 29, 2022.

(60) Provisional application No. 63/284,094, filed on Nov. 30, 2021.

(51) Int. Cl.
*A61B 34/30* (2016.01)
*A61B 34/00* (2016.01)

(52) U.S. Cl.
CPC .............. *A61B 34/30* (2016.02); *A61B 34/76* (2016.02)

(58) Field of Classification Search
CPC .................. A61B 34/30; A61B 34/76; A61B 2017/00973; A61B 2034/742; A61B 2090/065; A61B 90/361; A61B 34/37; A61B 50/13
See application file for complete search history.

(56) References Cited

U.S. PATENT DOCUMENTS

| 5,792,135 A | 8/1998 | Madhani et al. |
| 5,797,900 A | 8/1998 | Madhani et al. |
| 5,976,122 A | 11/1999 | Madhani et al. |
| 6,063,095 A | 5/2000 | Wang et al. |

(Continued)

FOREIGN PATENT DOCUMENTS

| CN | 105310775 A | 2/2016 |
| CN | 107427327 A | 12/2017 |

(Continued)

OTHER PUBLICATIONS

"Plenary 1: Colubris MX"—YouTube Video link address https://www.youtube.com/watch?v=in_luQiAZg8 dated Aug. 20, 2020.

(Continued)

*Primary Examiner* — Basil T. Jos
(74) *Attorney, Agent, or Firm* — Locke Lord LLP; Scott D. Wofsy

(57) ABSTRACT

A patient cart for a robot surgical system can include a mobile base having a frame adapted and configured to support a medical robot, one or more motive devices operatively connected to the frame, and one or more motors connected to the motive devices to drive the motive devices to move the frame. The patient cart can include a drive control interface connected to the frame and configured to sense a user input and to operate the one or more motors to move the one or more motive devices as a function of the user input.

7 Claims, 13 Drawing Sheets

(56) References Cited

U.S. PATENT DOCUMENTS

| | | | |
|---|---|---|---|
| 6,132,368 A | 10/2000 | Cooper | |
| 6,244,809 B1 | 6/2001 | Wang et al. | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,346,072 B1 | 2/2002 | Cooper | |
| 6,364,888 B1 | 4/2002 | Niemeyer et al. | |
| 6,371,952 B1 | 4/2002 | Madhani et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,451,027 B1 | 9/2002 | Cooper et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,522,906 B1 | 2/2003 | Salisbury, Jr. et al. | |
| 6,565,554 B1 | 5/2003 | Niemeyer | |
| 6,587,750 B2 | 7/2003 | Gerbi et al. | |
| 6,645,196 B1 | 11/2003 | Nixon et al. | |
| 6,671,581 B2 | 12/2003 | Niemeyer et al. | |
| 6,676,684 B1 | 1/2004 | Morley et al. | |
| 6,684,129 B2 | 1/2004 | Salisbury, Jr. et al. | |
| 6,699,177 B1 | 3/2004 | Wang et al. | |
| 6,699,235 B2 | 3/2004 | Wallace et al. | |
| 6,714,839 B2 | 3/2004 | Salisbury, Jr. et al. | |
| 6,746,443 B1 | 6/2004 | Morley et al. | |
| 6,766,204 B2 | 7/2004 | Niemeyer et al. | |
| 6,783,524 B2 | 8/2004 | Anderson et al. | |
| 6,785,593 B2 | 8/2004 | Wang et al. | |
| 6,799,088 B2 | 9/2004 | Wang et al. | |
| 6,817,972 B2 | 11/2004 | Snow | |
| 6,817,974 B2 | 11/2004 | Cooper et al. | |
| 6,836,703 B2 | 12/2004 | Wang et al. | |
| 6,837,846 B2 | 1/2005 | Jaffe et al. | |
| 6,840,938 B1 | 1/2005 | Morley et al. | |
| 6,852,107 B2 | 2/2005 | Wang et al. | |
| 6,866,671 B2 | 3/2005 | Tierney et al. | |
| 6,871,117 B2 | 3/2005 | Wang et al. | |
| 6,892,112 B2 | 5/2005 | Wang et al. | |
| 6,905,491 B1 | 6/2005 | Wang et al. | |
| 6,951,535 B2 | 10/2005 | Ghodoussi et al. | |
| 6,991,627 B2 | 1/2006 | Madhani et al. | |
| 6,994,703 B2 | 2/2006 | Wang et al. | |
| 7,025,064 B2 | 4/2006 | Wang et al. | |
| 7,027,892 B2 | 4/2006 | Wang et al. | |
| 7,048,745 B2 | 5/2006 | Tierney et al. | |
| 7,066,926 B2 | 6/2006 | Wallace et al. | |
| 7,074,179 B2 | 7/2006 | Wang et al. | |
| 7,083,571 B2 | 8/2006 | Wang et al. | |
| 7,087,049 B2 | 8/2006 | Nowlin et al. | |
| 7,090,637 B2 | 8/2006 | Danitz et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,204,844 B2 | 4/2007 | Jensen et al. | |
| 7,276,065 B2 | 10/2007 | Morley et al. | |
| 7,320,700 B2 | 1/2008 | Cooper et al. | |
| 7,331,967 B2 | 2/2008 | Lee et al. | |
| 7,333,642 B2 | 2/2008 | Green | |
| 7,357,774 B2 | 4/2008 | Cooper | |
| 7,398,707 B2 | 7/2008 | Morley et al. | |
| 7,524,320 B2 | 4/2009 | Tierney et al. | |
| 7,574,250 B2 | 8/2009 | Niemeyer | |
| 7,608,083 B2 | 10/2009 | Lee et al. | |
| 7,615,066 B2 | 11/2009 | Danitz et al. | |
| 7,691,098 B2 | 4/2010 | Wallace et al. | |
| 7,744,608 B2 | 6/2010 | Lee et al. | |
| 7,756,036 B2 | 7/2010 | Druke et al. | |
| 7,757,028 B2 | 7/2010 | Druke et al. | |
| 7,763,015 B2 | 7/2010 | Cooper et al. | |
| 7,780,651 B2 | 8/2010 | Madhani et al. | |
| 7,837,674 B2 | 11/2010 | Cooper | |
| 7,854,738 B2 | 12/2010 | Lee et al. | |
| 7,865,266 B2 | 1/2011 | Moll et al. | |
| 7,955,322 B2 | 6/2011 | Devengenzo et al. | |
| 8,052,636 B2 | 11/2011 | Moll et al. | |
| 8,054,752 B2 | 11/2011 | Druke et al. | |
| 8,068,649 B2 | 11/2011 | Green | |
| 8,075,474 B2 | 12/2011 | Honda et al. | |
| 8,100,133 B2 | 1/2012 | Mintz et al. | |
| 8,120,301 B2 | 2/2012 | Goldberg et al. | |
| 8,123,740 B2 | 2/2012 | Madhani et al. | |
| 8,147,503 B2 | 4/2012 | Zhao et al. | |
| 8,169,468 B2 | 5/2012 | Scott et al. | |
| 8,182,415 B2 | 5/2012 | Larkin et al. | |
| 8,190,238 B2 | 5/2012 | Moll et al. | |
| 8,228,368 B2 | 7/2012 | Zhao et al. | |
| 8,323,297 B2 | 12/2012 | Hinman et al. | |
| 8,335,590 B2 | 12/2012 | Costa et al. | |
| 8,337,521 B2 | 12/2012 | Cooper et al. | |
| 8,343,045 B2 | 1/2013 | Swinehart et al. | |
| 8,343,141 B2 | 1/2013 | Madhani et al. | |
| 8,365,633 B2 | 2/2013 | Simaan et al. | |
| 8,375,808 B2 | 2/2013 | Blumenkranz et al. | |
| 8,398,541 B2 | 3/2013 | DiMaio et al. | |
| 8,437,629 B2 | 5/2013 | McDowall | |
| 8,469,947 B2 | 6/2013 | Devengenzo et al. | |
| 8,475,366 B2 | 7/2013 | Boulais et al. | |
| 8,506,555 B2 | 8/2013 | Ruiz Morales | |
| 8,594,841 B2 | 11/2013 | Zhao et al. | |
| 8,597,280 B2 | 12/2013 | Cooper et al. | |
| 8,600,551 B2 | 12/2013 | Itkowitz et al. | |
| 8,617,102 B2 | 12/2013 | Moll et al. | |
| 8,644,988 B2 | 2/2014 | Prisco et al. | |
| 8,679,099 B2 | 3/2014 | Cooper et al. | |
| 8,690,908 B2 | 4/2014 | Cooper et al. | |
| 8,709,000 B2 | 4/2014 | Madhani et al. | |
| 8,740,885 B2 | 6/2014 | Larkin et al. | |
| 8,784,435 B2 | 7/2014 | Cooper et al. | |
| 8,786,241 B2 | 7/2014 | Nowlin et al. | |
| 8,790,243 B2 | 7/2014 | Cooper et al. | |
| 8,801,661 B2 | 8/2014 | Moll et al. | |
| 8,810,631 B2 | 8/2014 | Scott et al. | |
| 8,816,628 B2 | 8/2014 | Nowlin et al. | |
| 8,821,480 B2 | 9/2014 | Burbank | |
| 8,831,782 B2 | 9/2014 | Itkowitz | |
| 8,838,270 B2 | 9/2014 | Druke et al. | |
| 8,852,208 B2 | 10/2014 | Gomez et al. | |
| 8,887,595 B2 | 11/2014 | Williams | |
| 8,888,690 B2 | 11/2014 | Swinehart et al. | |
| 8,888,764 B2 | 11/2014 | Devengenzo et al. | |
| 8,903,549 B2 | 12/2014 | Itkowitz et al. | |
| 8,918,207 B2 | 12/2014 | Prisco | |
| 8,944,070 B2 | 2/2015 | Guthart et al. | |
| 8,945,095 B2 | 2/2015 | Blumenkranz et al. | |
| 9,011,318 B2 | 4/2015 | Choset et al. | |
| 9,050,120 B2 | 6/2015 | Swarup et al. | |
| 9,060,678 B2 | 6/2015 | Larkin et al. | |
| 9,089,354 B2 | 7/2015 | Simaan et al. | |
| 9,095,362 B2 | 8/2015 | Dachs, II et al. | |
| 9,138,284 B2 | 9/2015 | Krom et al. | |
| 9,144,456 B2 | 9/2015 | Rosa et al. | |
| 9,186,221 B2 | 11/2015 | Burbank | |
| 9,254,090 B2 | 2/2016 | Watson et al. | |
| 9,259,274 B2 | 2/2016 | Prisco | |
| 9,259,276 B2 | 2/2016 | Mintz et al. | |
| 9,301,807 B2 | 4/2016 | Duval | |
| 9,308,937 B2 | 4/2016 | Griffiths et al. | |
| 9,339,341 B2 | 5/2016 | Cooper | |
| 9,358,074 B2 | 6/2016 | Schena et al. | |
| 9,456,839 B2 | 10/2016 | Cooper | |
| 9,486,288 B2 | 11/2016 | Devengenzo et al. | |
| 9,498,242 B2 | 11/2016 | Crews et al. | |
| 9,504,517 B2 | 11/2016 | Rosa et al. | |
| 9,510,915 B2 | 12/2016 | Madhani et al. | |
| 9,565,990 B2 | 2/2017 | Lee et al. | |
| 9,687,310 B2 | 6/2017 | Nowlin et al. | |
| 9,717,486 B2 | 8/2017 | Cooper et al. | |
| 9,757,149 B2 | 9/2017 | Cooper et al. | |
| 9,757,203 B2 | 9/2017 | Hourtash et al. | |
| 9,775,678 B2 | 10/2017 | Lohmeier | |
| 9,782,056 B2 | 10/2017 | McDowall | |
| 9,782,225 B2 | 10/2017 | Lohmeier et al. | |
| 9,795,446 B2 | 10/2017 | DiMaio et al. | |

(56) References Cited

U.S. PATENT DOCUMENTS

| | | |
|---|---|---|
| 9,795,453 B2 | 10/2017 | Tierney et al. |
| 9,801,526 B2 | 10/2017 | Larkin et al. |
| 9,801,654 B2 | 10/2017 | Gomez et al. |
| 9,814,527 B2 | 11/2017 | Rogers et al. |
| 9,877,794 B2 | 1/2018 | Csiky |
| 9,901,402 B2 | 2/2018 | Itkowitz et al. |
| 9,918,659 B2 | 3/2018 | Chopra et al. |
| 9,949,620 B2 | 4/2018 | Duval et al. |
| 9,962,066 B2 | 5/2018 | Rogers et al. |
| 9,968,405 B2 | 5/2018 | Cooper et al. |
| 9,980,630 B2 | 5/2018 | Larkin et al. |
| 10,010,331 B2 | 7/2018 | Morash |
| 10,039,473 B2 | 8/2018 | Zhao et al. |
| 10,058,390 B2 | 8/2018 | Simaan et al. |
| 10,085,788 B2 | 10/2018 | Privitera et al. |
| 10,085,806 B2 | 10/2018 | Hagn et al. |
| 10,092,172 B2 | 10/2018 | Peh et al. |
| 10,105,128 B2 | 10/2018 | Cooper et al. |
| 10,117,715 B2 | 11/2018 | Lohmeier et al. |
| 10,159,536 B2 | 12/2018 | Kralicky et al. |
| 10,178,368 B2 | 1/2019 | Zhao et al. |
| 10,179,024 B2 | 1/2019 | Yeung |
| 10,179,413 B2 | 1/2019 | Rockrohr |
| 10,188,472 B2 | 1/2019 | Diolaiti et al. |
| 10,258,421 B2 | 4/2019 | Lohmeier et al. |
| 10,278,782 B2 | 5/2019 | Jarc et al. |
| 10,321,964 B2 | 6/2019 | Grover et al. |
| 10,327,856 B2 | 6/2019 | Kralicky et al. |
| 10,363,107 B2 | 7/2019 | Blumenkranz et al. |
| 10,365,295 B2 | 7/2019 | Blumenkranz et al. |
| 10,390,687 B2 | 8/2019 | Choi et al. |
| 10,390,895 B2 | 8/2019 | Henderson et al. |
| 10,391,635 B2 | 8/2019 | Berghofer et al. |
| 10,398,520 B2 | 9/2019 | Larkin et al. |
| 10,413,370 B2 | 9/2019 | Yates et al. |
| 10,448,813 B2 | 10/2019 | Cooper et al. |
| 10,456,166 B2 | 10/2019 | Cooper et al. |
| 10,507,068 B2 | 12/2019 | Kopp et al. |
| 10,512,481 B2 | 12/2019 | Cooper |
| 10,524,644 B2 | 1/2020 | Scott et al. |
| 10,524,868 B2 | 1/2020 | Cooper et al. |
| 10,531,929 B2 | 1/2020 | Widenhouse et al. |
| 10,602,958 B2 | 3/2020 | Silverstein et al. |
| 10,646,990 B2 | 5/2020 | Olds et al. |
| 10,660,713 B2 | 5/2020 | McCrea et al. |
| 10,682,193 B2 | 6/2020 | Choi et al. |
| 10,729,503 B2 | 8/2020 | Cameron |
| 10,736,702 B2 | 8/2020 | Harris et al. |
| 10,779,896 B2 | 9/2020 | Dachs, II et al. |
| 10,779,899 B2 | 9/2020 | Griffiths et al. |
| 10,786,329 B2 | 9/2020 | Schuh et al. |
| 10,820,953 B2 | 11/2020 | Kralicky et al. |
| 10,828,115 B2 | 11/2020 | Koenig et al. |
| 10,828,117 B2 | 11/2020 | Evans |
| 10,835,331 B2 | 11/2020 | Burbank |
| 10,835,335 B2 | 11/2020 | Perdue et al. |
| 10,856,946 B2 | 12/2020 | Solomon et al. |
| 10,864,051 B2 | 12/2020 | Simi et al. |
| 10,874,475 B2 | 12/2020 | Iceman |
| 10,898,189 B2 | 1/2021 | McDonald, II |
| 10,898,281 B2 | 1/2021 | Cooper et al. |
| 10,905,505 B1 | 2/2021 | Barakat et al. |
| 10,918,449 B2 | 2/2021 | Solomon et al. |
| 10,939,970 B2 | 3/2021 | Laakso et al. |
| 10,959,607 B2 | 3/2021 | Rogers et al. |
| 11,812,924 B2 * | 11/2023 | Garcia Kilroy ........ A61B 34/37 |
| 2002/0161281 A1 | 10/2002 | Jaffe et al. |
| 2003/0036748 A1 | 2/2003 | Cooper et al. |
| 2003/0083673 A1 | 5/2003 | Tierney et al. |
| 2003/0114962 A1 | 6/2003 | Niemeyer |
| 2003/0135203 A1 | 7/2003 | Wang et al. |
| 2004/0049205 A1 | 3/2004 | Lee et al. |
| 2004/0138700 A1 | 7/2004 | Cooper et al. |
| 2004/0162547 A1 | 8/2004 | Wallace et al. |
| 2004/0236316 A1 | 11/2004 | Danitz et al. |
| 2005/0043718 A1 | 2/2005 | Madhani et al. |
| 2005/0059960 A1 | 3/2005 | Simaan et al. |
| 2005/0149003 A1 | 7/2005 | Tierney et al. |
| 2005/0200324 A1 | 9/2005 | Guthart et al. |
| 2005/0204851 A1 | 9/2005 | Morley et al. |
| 2005/0216033 A1 | 9/2005 | Lee et al. |
| 2005/0251112 A1 | 11/2005 | Danitz et al. |
| 2006/0167440 A1 | 7/2006 | Cooper et al. |
| 2007/0043338 A1 | 2/2007 | Moll et al. |
| 2007/0137372 A1 | 6/2007 | Devengenzo et al. |
| 2007/0151390 A1 | 7/2007 | Blumenkranz et al. |
| 2007/0156119 A1 | 7/2007 | Wallace et al. |
| 2007/0156122 A1 | 7/2007 | Cooper |
| 2007/0197896 A1 | 8/2007 | Moll et al. |
| 2008/0065105 A1 | 3/2008 | Larkin et al. |
| 2008/0065107 A1 | 3/2008 | Larkin et al. |
| 2008/0065111 A1 | 3/2008 | Blumenkranz et al. |
| 2008/0071291 A1 | 3/2008 | Duval et al. |
| 2008/0077159 A1 | 3/2008 | Madhani et al. |
| 2008/0177282 A1 | 7/2008 | Lee et al. |
| 2008/0177284 A1 | 7/2008 | Lee et al. |
| 2008/0287963 A1 | 11/2008 | Rogers et al. |
| 2009/0023989 A1 | 1/2009 | Honda et al. |
| 2009/0171151 A1 | 7/2009 | Choset et al. |
| 2010/0011901 A1 | 1/2010 | Burbank |
| 2010/0048999 A1 | 2/2010 | Boulais et al. |
| 2010/0082041 A1 | 4/2010 | Prisco |
| 2010/0234831 A1 | 9/2010 | Hinman et al. |
| 2010/0274087 A1 | 10/2010 | Diolaiti et al. |
| 2010/0292708 A1 | 11/2010 | Madhani et al. |
| 2011/0118755 A1 | 5/2011 | Cooper et al. |
| 2011/0125166 A1 | 5/2011 | Cooper et al. |
| 2011/0144658 A1 | 6/2011 | Wenderow et al. |
| 2011/0152879 A1 | 6/2011 | Williams |
| 2011/0196419 A1 | 8/2011 | Cooper |
| 2011/0277580 A1 | 11/2011 | Cooper et al. |
| 2011/0282351 A1 | 11/2011 | Cooper et al. |
| 2011/0282359 A1 | 11/2011 | Duval |
| 2011/0282491 A1 | 11/2011 | Prisco et al. |
| 2011/0288561 A1 | 11/2011 | Devengenzo et al. |
| 2011/0313449 A1 | 12/2011 | Cooper |
| 2012/0150192 A1 | 6/2012 | Dachs, II et al. |
| 2012/0203271 A1 | 8/2012 | Larkin et al. |
| 2012/0209174 A1 | 8/2012 | Moll et al. |
| 2012/0221011 A1 | 8/2012 | Larkin et al. |
| 2012/0232339 A1 | 9/2012 | Csiky |
| 2013/0053868 A1 | 2/2013 | Cooper et al. |
| 2013/0079794 A9 | 3/2013 | Cooper et al. |
| 2013/0096540 A1 | 4/2013 | Cooper et al. |
| 2013/0110131 A1 | 5/2013 | Madhani et al. |
| 2013/0197539 A1 | 8/2013 | Simaan et al. |
| 2013/0197540 A1 | 8/2013 | Simaan et al. |
| 2013/0267950 A1 | 10/2013 | Rosa et al. |
| 2013/0267964 A1 | 10/2013 | Rogers et al. |
| 2013/0274761 A1 | 10/2013 | Devengenzo et al. |
| 2014/0081292 A1 | 3/2014 | Moll et al. |
| 2014/0194899 A1 | 7/2014 | Madhani et al. |
| 2014/0243852 A1 | 8/2014 | Cooper et al. |
| 2014/0257336 A1 | 9/2014 | Choi et al. |
| 2014/0277106 A1 | 9/2014 | Crews et al. |
| 2014/0296637 A1 | 10/2014 | Lee et al. |
| 2014/0296872 A1 | 10/2014 | Cooper et al. |
| 2015/0066002 A1 | 3/2015 | Cooper et al. |
| 2015/0100066 A1 | 4/2015 | Kostrzewski et al. |
| 2015/0150636 A1 | 6/2015 | Hagn et al. |
| 2015/0173726 A1 | 6/2015 | Lohmeier et al. |
| 2015/0173729 A1 | 6/2015 | Lohmeier et al. |
| 2015/0173731 A1 | 6/2015 | Lohmeier et al. |
| 2015/0173840 A1 | 6/2015 | Lohmeier |
| 2015/0238267 A1 | 8/2015 | Devengenzo et al. |
| 2015/0250546 A1 | 9/2015 | Larkin et al. |
| 2016/0015447 A1 | 1/2016 | Rosa et al. |
| 2016/0058512 A1 | 3/2016 | Gomez et al. |
| 2016/0066773 A1 | 3/2016 | Cooper et al. |
| 2016/0242860 A1 | 8/2016 | Diolaiti et al. |
| 2016/0256183 A1 | 9/2016 | Cooper |
| 2017/0014197 A1 | 1/2017 | McCrea et al. |
| 2017/0020615 A1 | 1/2017 | Koenig et al. |
| 2017/0071628 A1 | 3/2017 | Cooper et al. |

(56) References Cited

U.S. PATENT DOCUMENTS

| | | |
|---|---|---|
| 2017/0112505 A1 | 4/2017 | Morash |
| 2017/0156804 A1 | 6/2017 | Cooper et al. |
| 2017/0265923 A1 | 9/2017 | Privitera et al. |
| 2017/0273749 A1 | 9/2017 | Grover et al. |
| 2017/0274533 A1 | 9/2017 | Berghofer et al. |
| 2017/0281296 A1 | 10/2017 | Cooper et al. |
| 2017/0312043 A1 | 11/2017 | Ogawa et al. |
| 2017/0325879 A1 | 11/2017 | Yeung |
| 2017/0354318 A1 | 12/2017 | Rogers et al. |
| 2017/0367775 A1 | 12/2017 | Dachs, II et al. |
| 2017/0367777 A1 | 12/2017 | Kralicky et al. |
| 2018/0000318 A9 | 1/2018 | Rogers et al. |
| 2018/0000548 A1 | 1/2018 | Olds et al. |
| 2018/0014852 A1 | 1/2018 | Gomez et al. |
| 2018/0049820 A1 | 2/2018 | Widenhouse et al. |
| 2018/0049822 A1 | 2/2018 | Henderson et al. |
| 2018/0049827 A1 | 2/2018 | Harris et al. |
| 2018/0064498 A1 | 3/2018 | Kapadia et al. |
| 2018/0111273 A1 | 4/2018 | Linnell et al. |
| 2018/0132956 A1 | 5/2018 | Cameron |
| 2018/0168747 A1 | 6/2018 | Kopp et al. |
| 2018/0168752 A1 | 6/2018 | Scheib et al. |
| 2018/0193007 A1 | 7/2018 | Au et al. |
| 2018/0200894 A1 | 7/2018 | Rockrohr |
| 2018/0214176 A1 | 8/2018 | Solomon et al. |
| 2018/0221096 A1 | 8/2018 | Yates et al. |
| 2018/0242824 A1 | 8/2018 | Larkin et al. |
| 2018/0256270 A1 | 9/2018 | Cooper et al. |
| 2018/0271607 A1 | 9/2018 | Kralicky et al. |
| 2018/0271616 A1 | 9/2018 | Schuh et al. |
| 2018/0286287 A1 | 10/2018 | Razzaque |
| 2018/0296299 A1 | 10/2018 | Iceman |
| 2018/0317915 A1 | 11/2018 | McDonald, II |
| 2018/0318023 A1 | 11/2018 | Griffiths et al. |
| 2018/0324414 A1 | 11/2018 | Hoffman et al. |
| 2018/0353204 A1 | 12/2018 | Solomon et al. |
| 2018/0370045 A1 | 12/2018 | Kan |
| 2019/0039241 A1 | 2/2019 | Langenfeld et al. |
| 2019/0125467 A1 | 5/2019 | Evans |
| 2019/0216551 A1 | 7/2019 | Burbank |
| 2019/0269472 A1 | 9/2019 | Kralicky et al. |
| 2019/0274769 A1 | 9/2019 | Perdue et al. |
| 2019/0314645 A1 | 10/2019 | Ciresianu et al. |
| 2019/0328472 A1 | 10/2019 | Tojo et al. |
| 2019/0380801 A1 | 12/2019 | Savall et al. |
| 2020/0038123 A1 | 2/2020 | Graetzel et al. |
| 2020/0069389 A1 | 3/2020 | Morrissette et al. |
| 2020/0146763 A1 | 5/2020 | Schena et al. |
| 2020/0179067 A1 | 6/2020 | Ross et al. |
| 2020/0205917 A1 | 7/2020 | Peine et al. |
| 2020/0214774 A1 | 7/2020 | Yoshida et al. |
| 2020/0297444 A1 | 9/2020 | Camarillo et al. |
| 2020/0315615 A1* | 10/2020 | Yates .................... A61B 50/36 |
| 2020/0330173 A1 | 10/2020 | Kapadia et al. |
| 2020/0337725 A1 | 10/2020 | Kaufmann et al. |
| 2020/0367979 A1 | 11/2020 | Laakso et al. |
| 2020/0397456 A1 | 12/2020 | Kim et al. |
| 2021/0045819 A1 | 2/2021 | Castillo et al. |
| 2021/0187294 A1 | 6/2021 | Kaufmann et al. |
| 2021/0241542 A1 | 8/2021 | Shmayahu et al. |
| 2021/0259794 A1 | 8/2021 | Kato et al. |
| 2021/0267702 A1 | 9/2021 | Kim et al. |
| 2021/0322046 A1 | 10/2021 | Kim et al. |
| 2021/0338052 A1 | 11/2021 | Ouyang et al. |
| 2023/0101750 A1* | 3/2023 | Shelton, IV ........... A61B 18/00 606/41 |

FOREIGN PATENT DOCUMENTS

| | | |
|---|---|---|
| CN | 108309370 A | 7/2018 |
| CN | 109602499 A | 4/2019 |
| CN | 109674647 A | 4/2019 |
| CN | 110636811 A | 12/2019 |
| CN | 213606867 U | 7/2021 |
| EP | 2968048 B1 | 6/2018 |
| EP | 3175813 B1 | 1/2020 |
| EP | 3781367 A1 | 2/2021 |
| JP | 2019530517 A | 10/2019 |
| JP | 2020104843 A | 7/2020 |
| JP | 2021513442 A | 5/2021 |
| KR | 20110032444 A | 3/2011 |
| KR | 101943440 B1 | 1/2019 |
| WO | 2012/035492 A1 | 3/2012 |
| WO | 2016/109886 A1 | 7/2016 |
| WO | 2019055681 A1 | 3/2019 |
| WO | 2020243285 A1 | 12/2020 |
| WO | 2021026231 A1 | 2/2021 |
| WO | 2021071540 A1 | 4/2021 |
| WO | 2021161162 A1 | 8/2021 |
| WO | 2021161184 A1 | 8/2021 |

OTHER PUBLICATIONS

International Search Report and Written Opinion, of the Korean Intellectual Property Office, as ISA, mailed Apr. 6, 2023, in corresponding International Patent Application PCT/US2022/051217.

International Search Report and Written Opinion, of the Korean Intellectual Property Office, as ISA, mailed Apr. 6, 2023, in corresponding International Patent Application PCT/US2022/051220.

International Search Report and Written Opinion, of the Korean Intellectual Property Office, as ISA, mailed Apr. 7, 2023, in corresponding International Patent Application PCT/US2022/051225.

International Search Report and Written Opinion, of the Korean Intellectual Property Office, as ISA, mailed Apr. 6, 2023, in corresponding International Patent Application PCT/US2022/051237.

International Search Report and Written Opinion, of the Korean Intellectual Property Office, as ISA, mailed Apr. 6, 2023, in corresponding International Patent Application PCT/US2022/051246.

International Search Report and Written Opinion, of the Korean Intellectual Property Office, as ISA, mailed Apr. 6, 2023, in corresponding International Patent Application PCT/US2022/051255.

International Search Report and Written Opinion, of the Korean Intellectual Property Office, as ISA, mailed Apr. 6, 2023, in corresponding International Patent Application PCT/US2022/051259.

International Search Report and Written Opinion, of the Korean Intellectual Property Office, as ISA, mailed Apr. 6, 2023, in corresponding International Patent Application PCT/US2022/051261.

International Search Report and Written Opinion, of the Korean Intellectual Property Office, as ISA, mailed Apr. 14, 2023, in corresponding International Patent Application PCT/US2022/051265.

International Search Report and Written Opinion, of the Korean Intellectual Property Office, as ISA, mailed Apr. 6, 2023, in corresponding International Patent Application PCT/US2022/051262.

Office Action mailed Jun. 14, 2023, issued for Taiwanese Patent Application No. 111145622 and English translation of the Search Report.

Office Action mailed Mar. 8, 2024, issued for Taiwanese Patent Application No. 112148517 and Search Report.

* cited by examiner

MASTER CONTROL SYSTEMS FOR ROBOTIC SURGICAL SYSTEMS

CROSS-REFERENCE TO RELATED APPLICATIONS

This application is a continuation of International Patent Application No. PCT/US2022/051217 filed Nov. 29, 2022, which claims priority to and the benefit of U.S. Provisional Application No. 63/284,094, filed Nov. 30, 2021, the entire contents of which are herein incorporated by reference in their entirety.

FIELD

This disclosure relates to robotic surgical systems, e.g., for minimally invasive surgery including, but not limited to, endoluminal and single-site surgery.

BACKGROUND

Minimally invasive surgery such as endoluminal and single-site robotic surgery offer significant advantages versus traditional robotic surgery. For example, in endoluminal robotic surgery, no incision need be made to access difficult to access locations within a patient's natural lumen. This dramatically reduces and/or eliminates recovery time and improves procedural safety. A single-site system reduces incisions to a minimum single-site, which reduces an otherwise larger number of incisions to provide access for certain procedures.

Certain endoluminal and single-site robotic surgical systems have been proposed. Examples of such systems and related components can be found in U.S. Pat. No. 10,881,422, as well as U.S. Patent Application Nos. US20210322046, US20210322045, US20190117247, US20210275266, US20210267702, US20200107898, US20200397457, US202000397456, US20200315645, and US201962914226, all of the above being incorporated by reference herein in their entirety.

Conventional surgical robotics and systems have generally been considered satisfactory for their intended purpose. However, there is still a need in the art for improved robotic surgical systems, devices, methods, controls, and components, especially those configured for endoluminal and single-site surgery. The present disclosure provides improvements in such areas, for example.

SUMMARY

In accordance with at least one aspect of this disclosure, a robotic surgical system can include a patient cart having a mobile base configured to move relative to a floor, and one or more instrument controllers connected to the base for controlling a medical device for performing a surgical operation. The system can include a user console separate from the patient cart, the user console comprising one or more user inputs for controlling the one or more instrument controllers, and a patient cart motion control module configured to be connected to the mobile base and configured to monitor and/or control a position of the entire patient cart remotely.

The patient cart motion control module can be selectively connectable to the one or more user inputs such that control by the user inputs is switchable from the one or more instrument controllers to the mobile base. The patient cart motion control module and/or the mobile base can be configured to limit a rate of motion of the mobile base when the mobile base is controlled by the user console.

In certain embodiments, the system can include an indicator configured to indicate that the user console is operatively connected to the mobile base to control the mobile base. In certain embodiments, the one or more instrument controllers are configured for transluminal surgery.

In accordance with at least one aspect of this disclosure, a robotic surgical system can include one or more robotic instrument controllers configured to move and position a respective instrument having a respective end effector, a robotic camera controller configured to move and position a camera, and a robotic overtube controller configured to move and position an overtube. The one or more instruments can extend through the overtube such that the end effectors extend from a distal end of the overtube. The camera can extend through the overtube and extends from the distal end of the overtube.

The system can include a control module operatively connected to the one or more instrument controllers, the camera controller, and the overtube controller. The control module can be configured to receive one or more user inputs and to select between a plurality of modes as a function of the one or more user inputs. The modes can include an instrument control mode where the control module can be configured to cause the end effector to move by controlling the one or more robotic instrument controllers as a function of the position control signals. The modes can include a camera control mode where the control module is configured to cause the camera to move by controlling the robotic camera controller as a function of the position control signals. The modes can include an overtube control mode where the control module is configured to cause the overtube to move by controlling the robotic overtube controller, while the camera and the end effector connected mounted therewith are also moved, as a function of the position control signals.

The user inputs can include one or more input control devices (e.g., one or more hand control devices) configured for position control inputs. The user inputs can include one or more foot pedal devices and/or wherein the user inputs include one or more buttons on the one or more input control devices. In certain embodiments, the one or more input control devices can include a hand control device having a pistol grip, and the one or more mode selection controls include a mode selection button for each mode. In certain embodiments, the one or more input control devices can further include one or more foot pedals which can be configured to output a plurality of mode selection controls.

The control module can be configured to select one of the plurality of modes and operate in selected mode the based on a combination of user inputs or individual user inputs are operated. For example, the control module can be configured select one of the plurality of modes and control motion in the selected mode based on either a combination of hand control devices and a foot pedal, or a combination of hand control devices and a button on the hand control devices.

The system can include a display configured to display images from the camera. The displayed image can be changed in response to the movement of the end effector. In certain embodiments, the control module can be configured to automatically move the camera in the instrument control mode to correlate motion to the end effector.

The displayed image can be changed in response to the movement of the camera. In certain embodiments, the displayed image can be changed in response to the movement of the overtube.

In accordance with at least one aspect of this disclosure, a control module for a robotic surgical system can be configured to receive one or more user inputs and to select between a plurality of modes as a function of the one or more user inputs. The modes can include any suitable modes disclosed herein, e.g., as described above. The control module can be or include any suitable module(s) disclosed herein, e.g., as described above.

In accordance with at least one aspect of this disclosure, a patient cart for a robot surgical system can include a mobile base having a frame adapted and configured to support a medical robot, one or more motive devices operatively connected to the frame, and one or more motors connected to the motive devices to drive the motive devices to move the frame. The patient cart can include a drive control interface connected to the frame and configured to sense a user input and to operate the one or more motors to move the one or more motive devices as a function of the user input.

In certain embodiments, the drive control interface can include one or more grip actuators configured to be actuated by a user. In certain embodiments, the drive control interface can include two grip actuators. In certain embodiments, the drive control interface can include a housing defining a handle recess. In certain embodiments, the one or more grip actuators can be disposed within the handle recess.

The drive control interface can include a drive control module operatively connected to one or more grip actuators to receive one or more state signals from the one or more grip actuators indicative of a position of the one or more grip actuators. The drive control module can be configured to allow operation of the one or more motors in a drive mode if the one or more grip actuators are partially pressed.

The drive control module can be configured to prevent operation of the one or more motors if the one or more grip actuators are pressed to or beyond a stop threshold. In certain embodiments, the stop threshold is complete actuation of the one or more grip actuators. In certain embodiments, the drive control interface can include a force sensor configured to sense a force and directionality of a user input.

The drive control module is operatively connected to the force sensor to receive a sensed force, wherein in the drive mode, the drive control module is configured to operate the one or more motors as a function of the sensed force such that the one or more motors cause motion in a direction of the sensed force.

The drive control module can be configured to operate the one or more motors at a speed proportional to the sensed force, for example. In certain embodiments, the patient cart can include a battery and can be operatively connected to the one or more motors to provide motive energy to the one or more motors to allow motion of the patient cart without an external power supply.

In accordance with at least one aspect of this disclosure, a method for driving a patient cart of a robotic surgical system can include partially depressing one or more grip actuators on a drive control interface to initiate a drive mode, and applying force on a patient cart handle in a desired direction of motion thereby causing one or more motors to drive the patient cart in the desired direction of motion. In certain embodiments, applying force includes pushing the patient cart handle in a forward direction while partially depressing the one or more grip actuators to move the patient cart forward.

In certain embodiments, applying force can include pulling on the patient cart handle in a rearward direction while partially depressing the one or more grip actuators to move the patient cart backward. In certain embodiments, the method can include either fully depressing or releasing the drive control switch to stop motion of the patient cart. In certain embodiments, applying force can include pushing or pulling on the patient cart handle in a lateral direction while partially depressing the one or more grip actuators to steer the patient cart.

In accordance with at least one aspect of this disclosure, a robotic surgical system can include one or more robotic instrument controllers configured to move and position a respective instrument having a respective end effector, a robotic camera controller configured to move and position a camera, and a robotic overtube controller configured to move and position an overtube. The one or more instruments can extend through the overtube such that the end effectors extend from a distal end of the overtube. The camera can extend through the overtube and extend from the distal end of the overtube. The system can include one or more input control devices having a plurality of mode selection controls thereon configured to output one or more input control mode signals, and configured to receive user inputs and output position control signals.

The system can include a control module operatively connected to the one or more instrument controllers, the camera controller, and the overtube controller, and can be configured to receive the one or more input control mode signals from the one or more input control devices, and to select between a plurality of modes as a function of the one or more input control mode signals. The modes can include an instrument control mode wherein the control module is configured cause the end effector to move by controlling the one or more robotic instrument controllers as a function of the position control signals, a camera control mode wherein the control module is configured to cause the camera to move by controlling the robotic camera controller as a function of the position control signals, and an overtube control mode wherein the control module is configured to cause the overtube to move by controlling the robotic overtube controller, while the camera and the end effector mounted therewith are also moved by virtue of the motion of the overtube, as a function of the position control signals.

In certain embodiments, the one or more input control device can include a pistol grip, for example. In certain embodiments, the one or more mode selection controls can include a mode selection button for each mode.

In accordance with at least one aspect of this disclosure, a control module for a robotic surgical system can be configured to receive one or more user inputs and to select between a plurality of modes as a function of the one or more user inputs, wherein the modes include an instrument control mode wherein the control module is configured cause an end effector to move by controlling one or more robotic instrument controllers as a function of the position control signals, a camera control mode wherein the control module is configured to cause a camera to move by controlling a robotic camera controller as a function of the position control signals, and an overtube control mode wherein the control module is configured to cause the overtube to move by controlling a robotic overtube controller, while the camera and the end effector mounted therewith are also moved by virtue of the motion of the overtube, as a function of the position control signals, a 2-dimensional imaging mode configured to output a 2-dimensional image from the camera, and a 3-dimensional imaging mode configured to output a 3-dimensional image from the camera. Any other additional suitable modes are contemplated herein.

In certain embodiments, the robotic surgical system further comprises one or more instrument controllers configured to move and position a respective instrument having a respective end effector, a robotic camera controller configured to move and position a camera, a robotic overtube controller configured to move and position an overtube and one or more input control device having a plurality of mode selection controls thereon configured to output one or more input control mode signals, and configured to receive user inputs and output position control signals. In certain embodiments, the control module is in communication with the one or more instrument controllers, the robotic camera controller, or the robotic overtube controller to operate the one or more instrument controllers, the robotic camera controller, or the robotic overtube controller as a function of the one or more input control mode signals.

These and other features of the embodiments of the subject disclosure will become more readily apparent to those skilled in the art from the following detailed description taken in conjunction with the drawings.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

Figure 1:
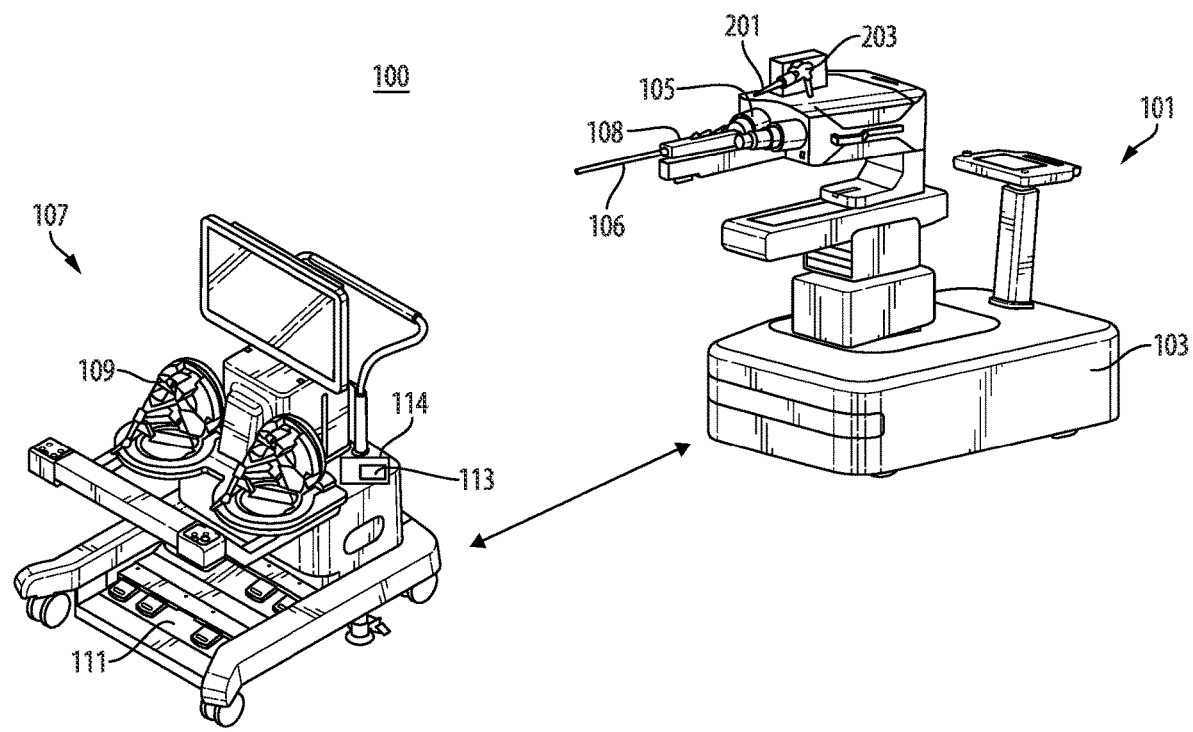
FIG. 1 is a perspective view of an embodiment of a robotic surgical system in accordance with this disclosure, showing a user console wirelessly connected to a patient cart.

Reference will now be made to the drawings wherein like reference numerals identify similar structural features or aspects of the subject disclosure. For purposes of explanation and illustration, and not limitation, an illustrative view of an embodiment of a system in accordance with the disclosure is shown in FIG. 1 and is designated generally by reference character 100. Other embodiments and/or aspects of this disclosure are shown in FIGS. 1A-12B.

Figure 1A:
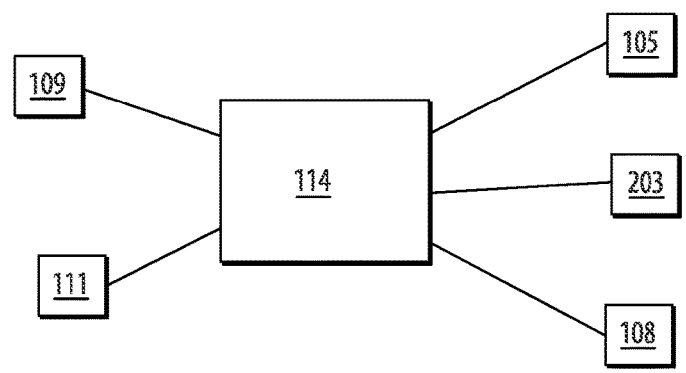
FIG. 1A is a schematic diagram of an embodiment of a control system in accordance with this disclosure.
Figure 1B:
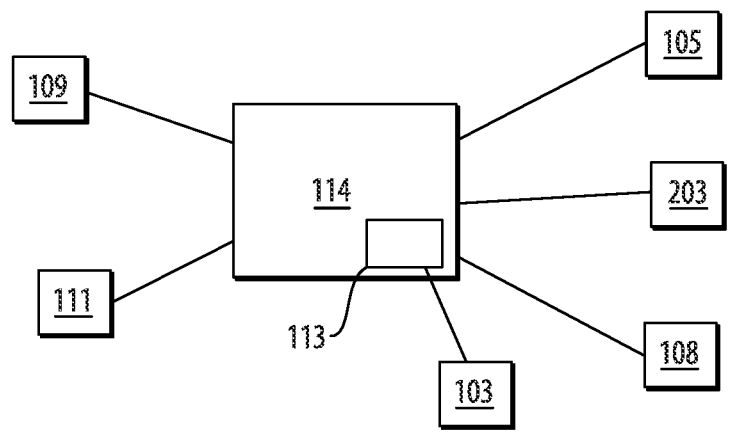
FIG. 1B is a schematic diagram of an embodiment of a control system in accordance with this disclosure.

Referring to FIGS. 1, 1A, and 1B, and generally to FIGS. 2-12B, in accordance with at least one aspect of this disclosure, a robotic surgical system 100 can include a patient cart 101 having a mobile base 103 configured to move relative to a floor (e.g., via one or more motorized wheels 103A and 103B and/or any other suitable motive system). The system 100 can include one or more instrument controllers 105 (e.g, configured to connect to a medical device such as a robotically controlled forceps assembly attachable to an instrument controller 105) for controlling a medical device and/or an overtube 106 for performing a surgical operation. For example, the instrument controllers 105 can be configured to control a position and/or state of a medical device. The one or more instrument controllers 105 can be connected to the base 103 (e.g., via a positioning system having one or more positioning devices for moving the instrument controllers 105 relative to the base 103).

The system 100 can include a user console 107 separate from the patient cart 101, the user console 107 comprising one or more user inputs (e.g., hand inputs 109, foot pedals 111) for controlling the one or more instrument controllers 105. The user console 107 can include a patient cart motion control module 113 configured to be connected to the mobile base 103 and configured to monitor and/or control a position of the entire patient cart 101 remotely (e.g., by controlling one or more motorized wheels of the mobile base 103). The patient cart motion control module 113 can include any suitable hardware and/or software configured to perform any suitable function (e.g., as disclosed herein). The patient cart motion control module 113 can be included as part of any suitable control hardware and/or software module(s) 113 (e.g., commonly hosted with instrument controller software), and/or can be an independent module (of any suitable parts) in any suitable manner. For example, module 113 can be included in a control module 114, e.g., as described below. The user console 107 can be connected via a wireless or a wired connection to the patient cart 103.

In certain embodiments, the patient cart motion control module 113 can be selectively connectable to the one or more user inputs 109, 111 such that control by the user inputs 109, 111 is switchable from the one or more instrument controllers 105 to the mobile base 103. It is contemplated that the user console 107 can also/alternatively include dedicated controls for the base 103. Any suitable switch, physical or digital, is contemplated herein.

The patient cart motion control module 113 and/or the mobile base 103 can be configured to limit a rate of motion of the mobile base 103 when the mobile base 103 is controlled by the user console 107 (e.g., via the patient cart motion control module 113). This can improve safety. In certain embodiments, the system 100 can include an indicator configured to indicate that the user console 107 is operatively connected to the mobile base 103 to control the mobile base 103.

The user console 107 can be connected to the patient cart 101 in any suitable manner for each to send and/or receive signals. For example, the patient cart 101 can include a receiver module configured to receive command signals from the user console, the receiver module configured to interpret any command signals and execute the commands. In certain embodiments, however, the user console 107 can be in direct communication with one or more (e.g., each) subsystem of the patient cart 101 and can be configured to directly control one or more (e.g., each) subsystem of the patient cart 101 with direct command signals. For example, the user console 107 can include a control module (e.g., including module 113) that it in communication with the one or more instrument controllers 105 and/or the mobile base 103 to control a position of the patient cart 101 and/or a surgical instrument directly. Any suitable configuration for commands from the user console 107 to ultimately control the patient cart 101 and/or one or more subsystems, directly or indirectly, is contemplated herein.

Figure 10:
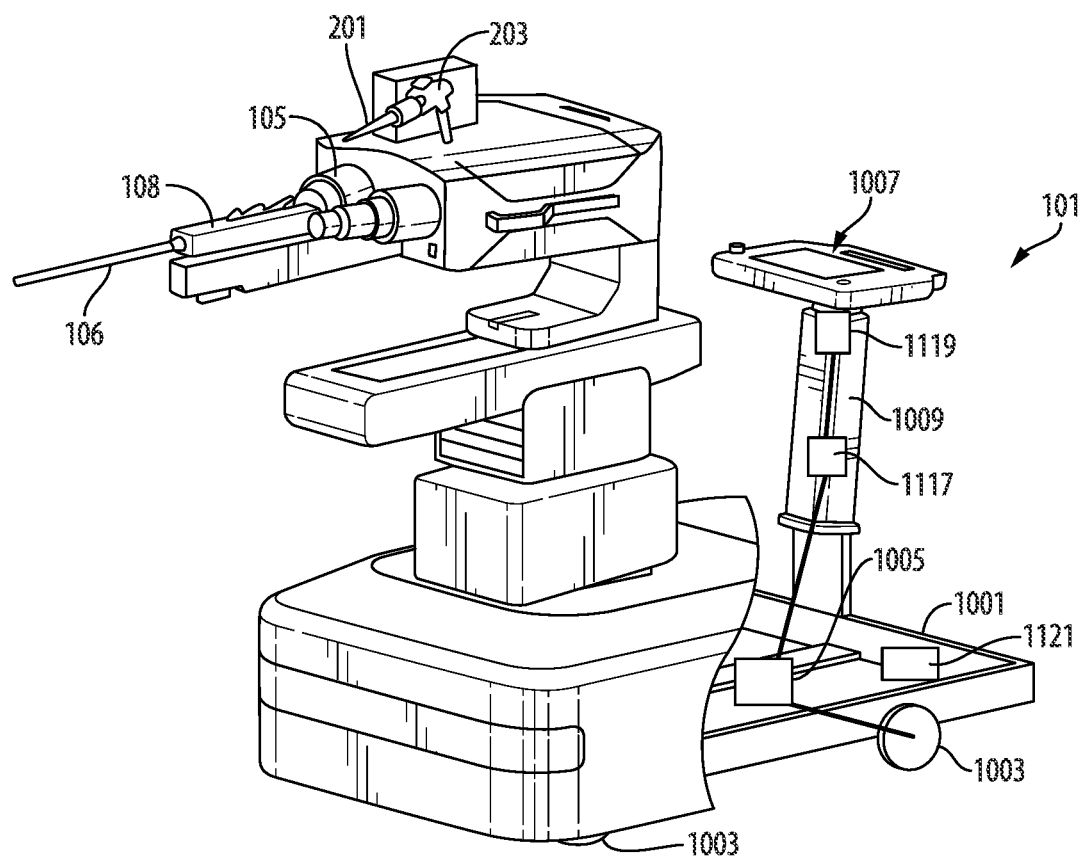
FIG. 10 shows an embodiment of a patient cart in accordance with this disclosure.

In accordance with at least one aspect of this disclosure, referring to FIG. 10, a patient cart 101 (which can also be referred to as a base cart herein) for a robotic surgical system 100 can include a mobile base 103 having a frame 1001 adapted and configured to support a medical robot (e.g., a robotic system as disclosed herein). The patient cart 101 can include one or more motive devices 1003 operatively connected to the frame 1001. The frame 1001 can include any suitable structural shape (e.g., a rectangular vehicle chassis formed of cross members, etc.). The term "motive devices" as used herein can include any suitable type of motive mechanism such as wheels, tracks, or any other suitable drivable member that can cause motion of the frame 1001 relative to a surface.

The patient cart 101 can include one or more motors 1005 connected to the one or more motive devices 1003 to drive the motive devices 1003 to move the frame 1001. The one or more motors 1005 can be one or more electric motors connected to the motive devices 1003 via a motor shaft for example. Any suitable number of motors 1005 is contemplated herein. For example, there can be a motor 1005 for each motive device 1003 (e.g., four wheels similar to a car) such that each motive device 1003 is associated with a respective motor 1005 and multi-motive device steering is enabled.

Figure 11:
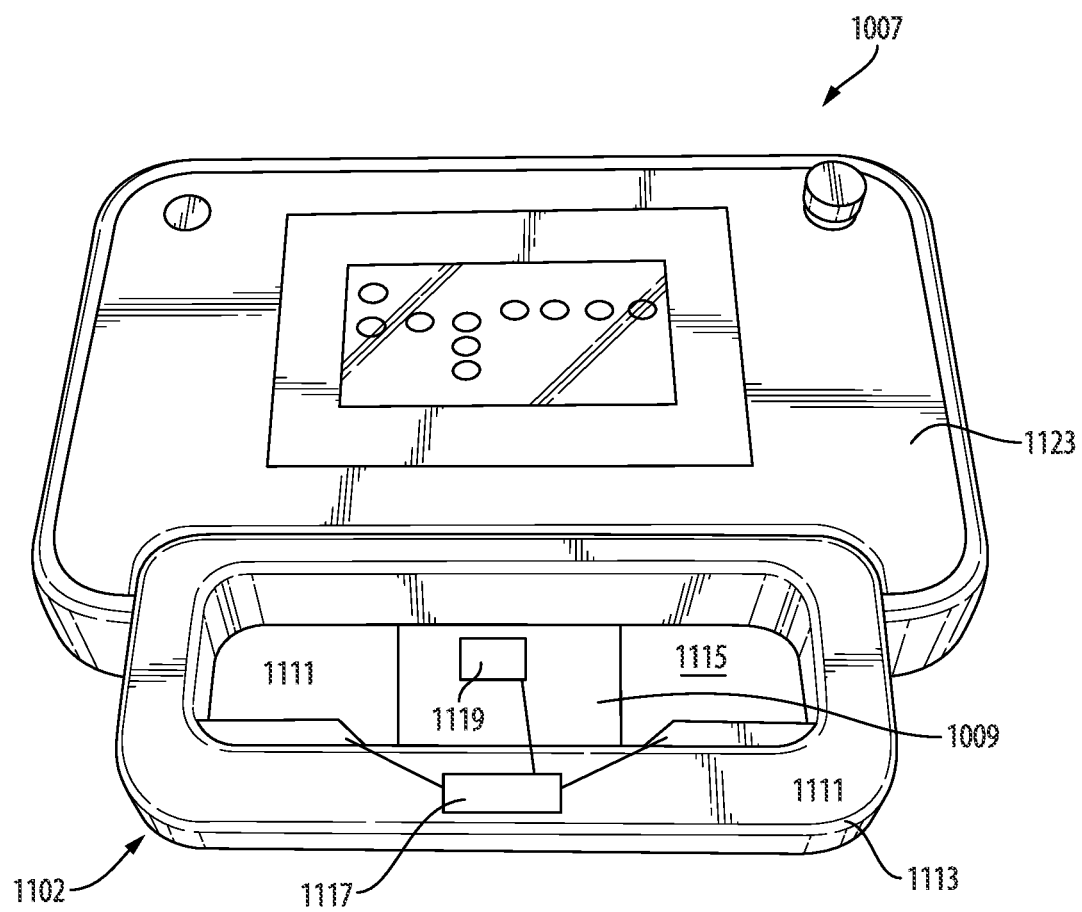
FIG. 11 is a perspective view of the patient cart of FIG. 10, illustrating an embodiment of a drive control interface in accordance with this disclosure.

Referring additionally to FIG. 11, the patient cart 101 can include a drive control interface 1007 connected to the frame 1001 (e.g., via a post 1009) and can be configured to sense a user input (e.g., a pushing force and or a pulling force). The drive control interface 1007 can be configured to operate the one or more motors 1005 to move the one or more motive devices 1003 as a function of the user input.

In certain embodiments, the drive control interface 1007 can include one or more grip actuators 1101 configured to be actuated by a user. In certain embodiments, the drive control interface 1007 can include two grip actuators 1101, e.g., as shown. In certain embodiments, the drive control interface 1007 can include a housing 1113 defining a handle recess 1115. In certain embodiments, the one or more grip actuators 1111 can be disposed within the handle recess 1115, e.g., as shown.

The drive control interface 1007 can include a drive control module 1117 operatively connected to one or more grip actuators 1111 to receive one or more state signals from the one or more grip actuators 1111 indicative of a position (e.g., half pressed, completely pressed) of the one or more grip actuators 1111. The drive control module 1117 can be configured to allow operation of the one or more motors 1005 (and/or operate the one or more motors 1005) in a drive mode if the one or more grip actuators 1111 are partially pressed (e.g., half way pressed). This can require a certain tactile precision to enable the drive mode to avoid accidental movement of the patient cart 101 by a user. In certain embodiments, the drive control module 1117 can be configured to allow operation of the one or more motors 1005 with any suitable partial or complete actuation of the one or more grip actuators 1111.

The drive control module 1117 can be configured to prevent operation of the one or more motors if the one or more grip actuators 1111 are pressed to or beyond a stop threshold. In certain embodiments, the stop threshold is complete actuation of the one or more grip actuators 1111. In certain embodiments, the drive control interface 1007 can include a force sensor 1119 configured to sense a force (e.g., a force and/or a torque) and directionality of a user input (e.g., a pushing force, a pulling force, and/or a torque).

The drive control module 1117 can be operatively connected to the force sensor 1119 to receive a sensed force. In the drive mode, the drive control module 1117 can be configured to operate the one or more motors 1005 as a function of the sensed force such that the one or more motors 1005 cause motion in a direction of the sensed force.

The drive control module 1117 can be configured to operate the one or more motors 1005 at a speed proportional to the sensed force, for example. This can provide a logical relationship between how hard a user presses, pulls, or turns, and the actual rate of motion of the patient cart 101. In certain embodiments, the speed can be linearly proportional, and in certain embodiments, the speed can be non-linearly proportional. Other relationships between sensed force and operating speed of the motors are contemplated herein.

In certain embodiments, the patient cart 101 can include a battery 1121 and can be operatively connected to the one or more motors 1005 (connection not shown) to provide motive energy to the one or more motors 1005 to allow motion of the patient cart 101 without an external power supply. In certain embodiments, the cart 101 may include or require an external power supply.

The drive control interface 1007 can include any suitable structure. The drive control module 1117 and the force sensor 1119 can be integrated within any suitable structure of the drive control interface 1007 and/or any other suitable portion of the patient cart 101. For example, the drive control interface 1007 can include a control pad 1123 as shown mounted (fixedly or removably) to a post 1009. The force sensor 1119 can be placed between the control pad 1123 and the post 1009, for example. In certain embodiments, the force sensor 1119 can be placed between the post 1009 and the frame 1001, for example. The drive control module 1117 can be placed within the control pad 1123 and/or within the post 1009, and/or within any other suitable portion of the patient cart 101. The control pad 1123 can include a touchscreen 1124 having one or more controls thereon to control any other suitable portion of the patient cart 101 (e.g., an instrument positioning system of the patient cart 101).

In accordance with at least one aspect of this disclosure, a method for driving a patient cart 101 of a robotic surgical system can include partially depressing one or more grip actuators 1101 on a drive control interface 1007 to initiate a drive mode, and applying force on a patient cart handle 1102 in a desired direction of motion thereby causing one or more motors 1005 to drive the patient cart 101 in the desired direction of motion. In certain embodiments, applying force includes pushing the patient cart handle 1102 in a forward direction while partially depressing the one or more grip actuators 1101 to move the patient cart 101 forward.

In certain embodiments, applying force can include pulling on the patient cart handle 1102 in a rearward direction while partially depressing the one or more grip actuators 1101 to move the patient cart 101 backward. In certain embodiments, the method can include either fully depressing or releasing the drive control switch to stop motion of the patient cart 101. In certain embodiments applying force can include pushing or pulling on the patient cart handle 1102 in a lateral direction while partially depressing the one or more grip actuators 1101 to steer the patient cart 101.

In certain embodiments, the patient cart can have a rechargeable battery 1121 and can be moved without an external power supply. The patient cart 101 can be moved by pressing the drive control switches (e.g., grip actuators 1101), for example. In certain embodiments, the patient cart 101 can be moved to any direction by pressing the drive control switch on the patient cart handle 1102 half-way and applying force to the direction to move. The patient cart drive control switch can be used for controlled movements of the patient cart 101 and can function such that when completely pressed, the patient cart 101 is stopped, and when half-way pressed, the patient cart is activated in drive mode.

A method for driving the patient cart 101 can include pressing and holding the drive control switch half-way-through and applying force on the patient cart handle 1102 in the required direction of motion. For example, to move forward, a user can apply force to the patient cart handle 1102 in forward direction (i.e., push) while holding the drive control switch half-way-through. Similarly, a user can apply force in the other direction (i.e., pull) to move the cart backward. In certain embodiments, the user can release the drive control switch or press completely to stop acceleration of the patient cart movement.

In certain embodiments, the one or more instrument controllers 105 are configured for transluminal surgery, for example. Any suitable instrument controller(s) 105 are contemplated herein.

Figure 7:
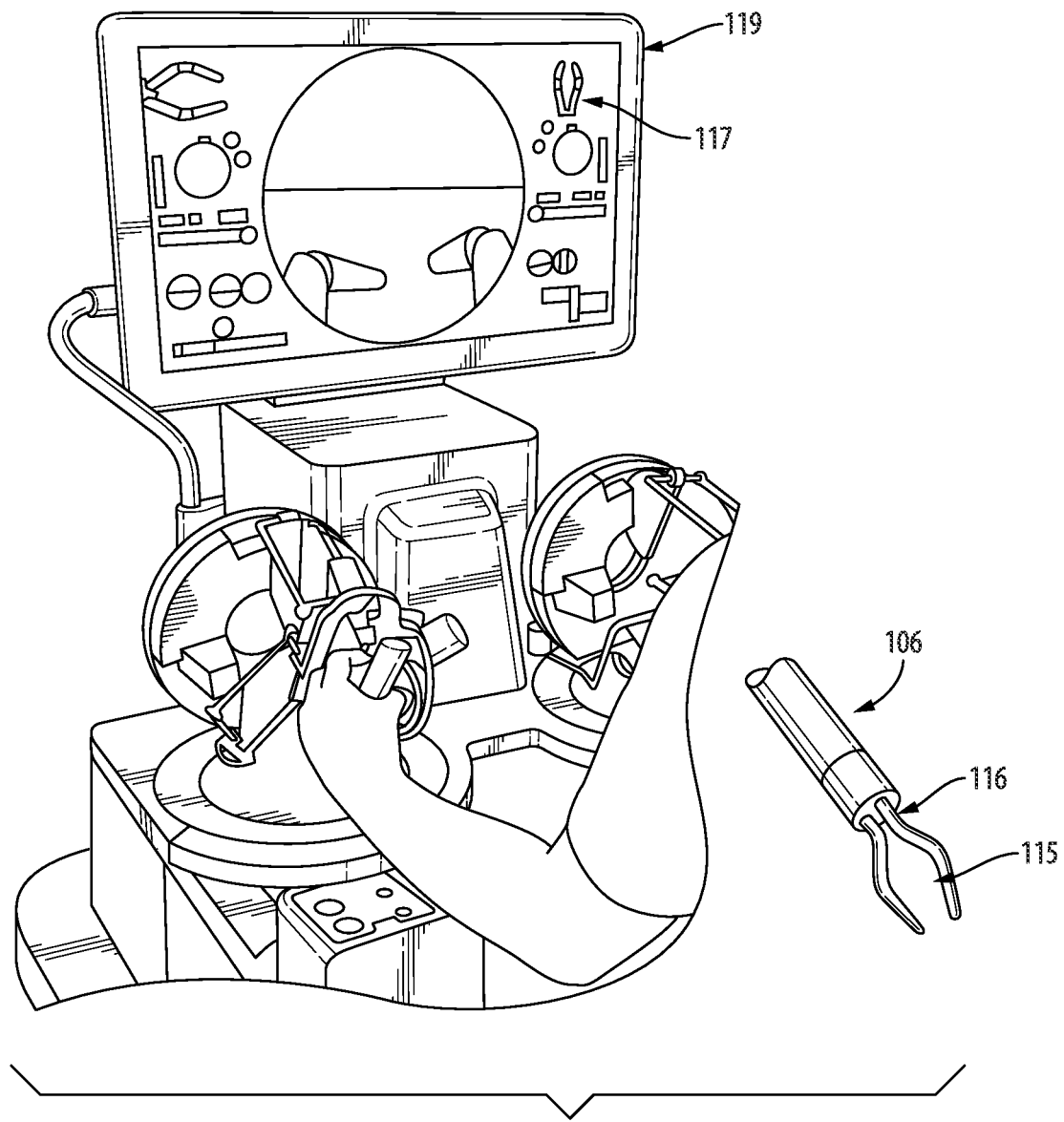
FIG. 7 shows a user using inputs on the patient cart, and a display thereof displaying a graphical user interface.

In accordance with at least one aspect of this disclosure, a robotic surgical system 100 can include one or more robotic instrument controllers 105 configured to move and position a respective instrument having a respective end effector (e.g., end effector 115 as shown in FIG. 7), a robotic camera controller 203 configured to move and position a camera 201 (e.g., a videoscope), and a robotic overtube controller 108 configured to move and position an overtube 106. The one or more instruments can extend through the overtube such that the end effectors 115 extend from a distal end of the overtube 106. The camera 201 can extend through the overtube 106 and extends from the distal end of the overtube 106 (e.g., as shown in FIG. 7).

The system 100 can include a control module 114 operatively connected to the one or more instrument controllers 105, the camera controller 203, and the overtube controller 108 (e.g., as shown in FIGS. 1A and 1B). The control module 114 can be configured to receive one or more mode control signals (e.g., via hand inputs 109 and/or pedals 111) and to select between a plurality of modes as a function of the one or more mode control signals. The control module 114 can include any suitable hardware and/or software configured to perform any suitable function (e.g., as disclosed herein). The control module 114 can be included as part of any suitable control hardware and/or software module(s), and/or can be an independent module (of any suitable parts) in any suitable manner. The control module 114 can be connected via a wireless or a wired connection to any suitable component.

In certain embodiments, the control module 114 does not include module 113, e.g., as shown in FIG. 1A. In certain embodiments, the control module 114 includes module 113, e.g., as show in FIG. 1B.

The modes can include an instrument control mode where the control module 114 can be configured to cause the end effector 115 to move by controlling the one or more robotic instrument controllers 105 as a function of the position control signals. The modes can include a camera control mode where the control module 114 is configured to cause the camera 201 to move by controlling the robotic camera controller 203 (e.g., while the end effector 115 is locked, or otherwise) as a function of the position control signals. The modes can include an overtube control mode where the control module 114 is configured to cause the overtube 106 to move by controlling the robotic overtube controller 108, while the camera 201 and the end effector 115 connected mounted therewith are also moved, as a function of the position control signals.

The user inputs can include one or more input control devices (e.g. hand control devices such as hand inputs 109) configured for position control inputs. The user inputs can include one or more foot pedal devices 111 and/or the user inputs can include one or more buttons (e.g., a finger trigger described below) on the one or more input control device 109.

The control module 114 can be configured to select one of the plurality of modes and operate in the selected mode based on a combination of user inputs or individual user inputs. For example, the control module 114 can be configured select one of the plurality of modes and control motion in the selected mode based on either a combination of input control device 109 and a foot pedal 111, or a combination of input control device 109 and a button on the input control device 109. Certain embodiments of control processes are disclosed below. Any other suitable control process and/or commands to switch and/or operate in each mode is contemplated herein.

The system 100 can include a display 119 configured to display images from the camera 201. The displayed image (e.g, the view of the camera) can be changed in response to the movement of the end effector such that the control module is configured to correlate motion of the camera to the end effector. The displayed image (e.g, the view of the camera and/or a GUI) can be changed in response to the movement of the end effector 115. In certain embodiments, the control module 114 can be configured to automatically move the camera 201 in the instrument control mode to correlate motion to the end effector 115.

The displayed image (e.g, the view of the camera and/or a GUI) can be changed in response to the movement of the camera 201. In certain embodiments, the displayed image (e.g, the view of the camera and/or a GUI) can be changed in response to the movement of the overtube 106.

In accordance with at least one aspect of this disclosure, a control module 114 for a robotic surgical system 100 can be configured to receive one or more mode control signals and to select between a plurality of modes as a function of the one or more mode control signals. The modes can include any suitable modes disclosed herein, e.g., as described above. The control module 114 can be or include any suitable module(s) disclosed herein, e.g., as described above.

The system 100 and/or any suitable portion(s) thereof can include any suitable component(s) disclosed herein. The system 100 can be configured for use as disclosed herein and/or in any other suitable manner.

Figure 2:
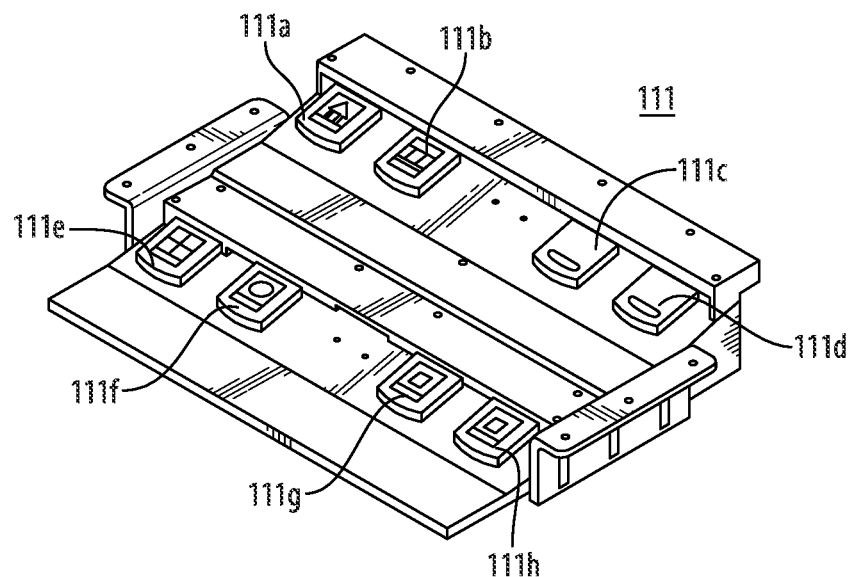
FIG. 2 shows an embodiment of a foot pedal arrangement of the embodiment of a user console shown in FIG. 1.

FIG. 1 is a perspective view of an embodiment of a robotic surgical system in accordance with this disclosure, showing a user console wirelessly connected to a patient cart. FIG. 2 shows an embodiment of a foot pedal arrangement of the embodiment of a user console shown in FIG. 1. FIG. 1A is a schematic diagram of an embodiment of a control system, showing hand inputs 109 (e.g., one or more input control device), 111 (e.g., one or more foot pedals) connected to the control module 114, and the control module 114 connected to the controllers 105, 108, and 203 for controlling the controllers in a respective mode as disclosed herein. FIG. 1B is a schematic diagram of an embodiment of a control system shown having module 113 controllable in an additional mode.

Figure 3:
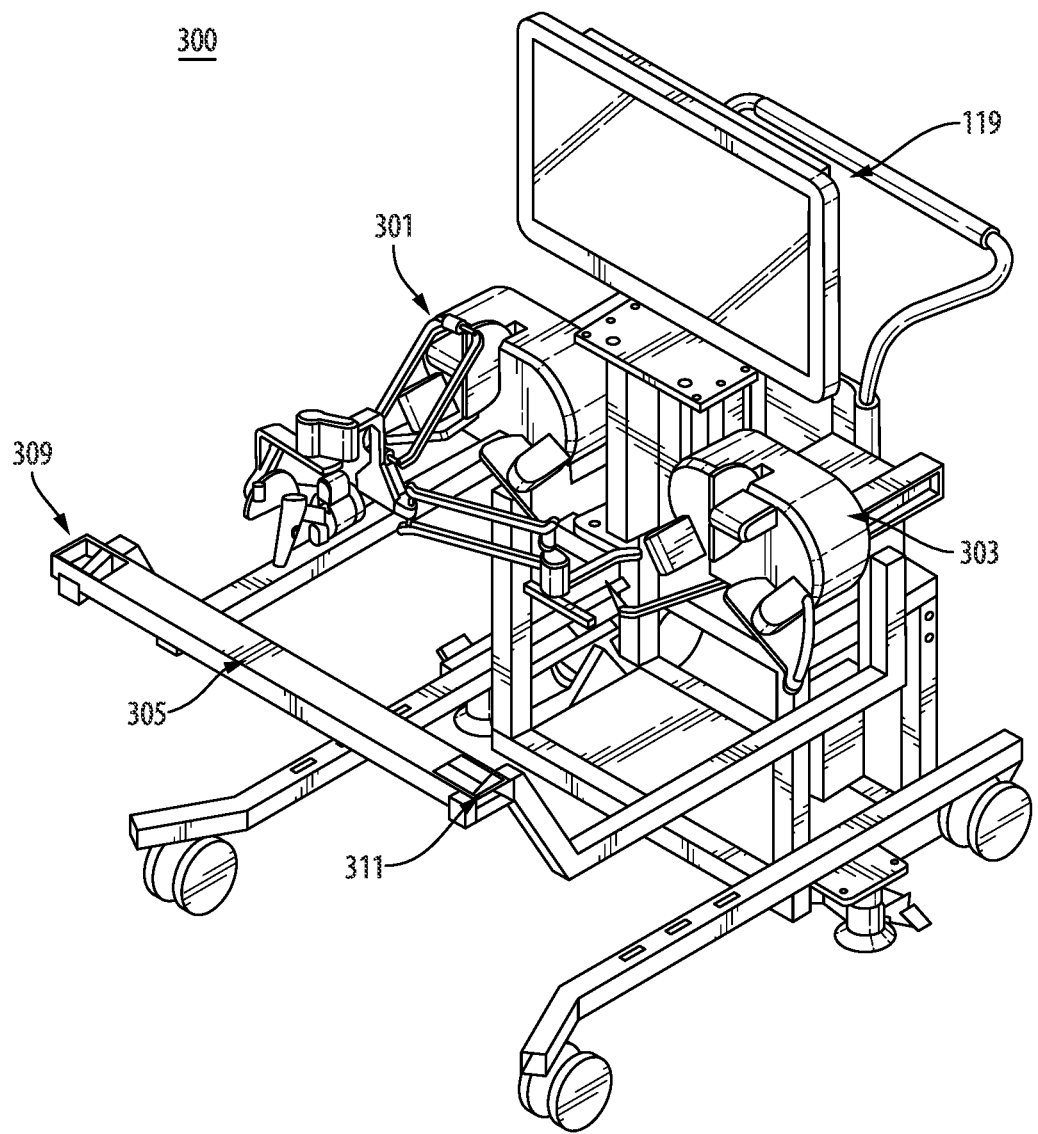
FIG. 3 is a perspective view of another embodiment of a user console in accordance with this disclosure.
Figure 4:
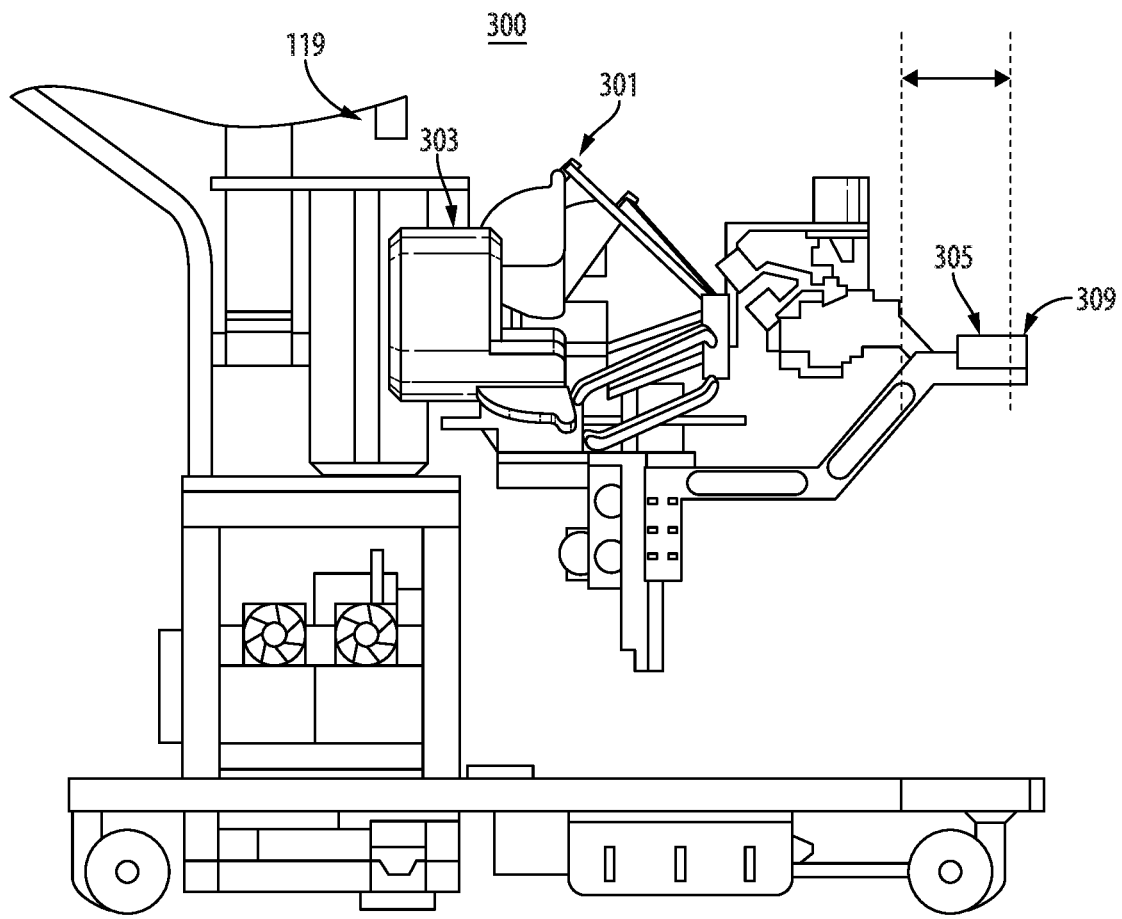
FIG. 4 is an elevation view of the embodiment of FIG. 3, showing horizontal arm rest adjustability.
Figure 5:
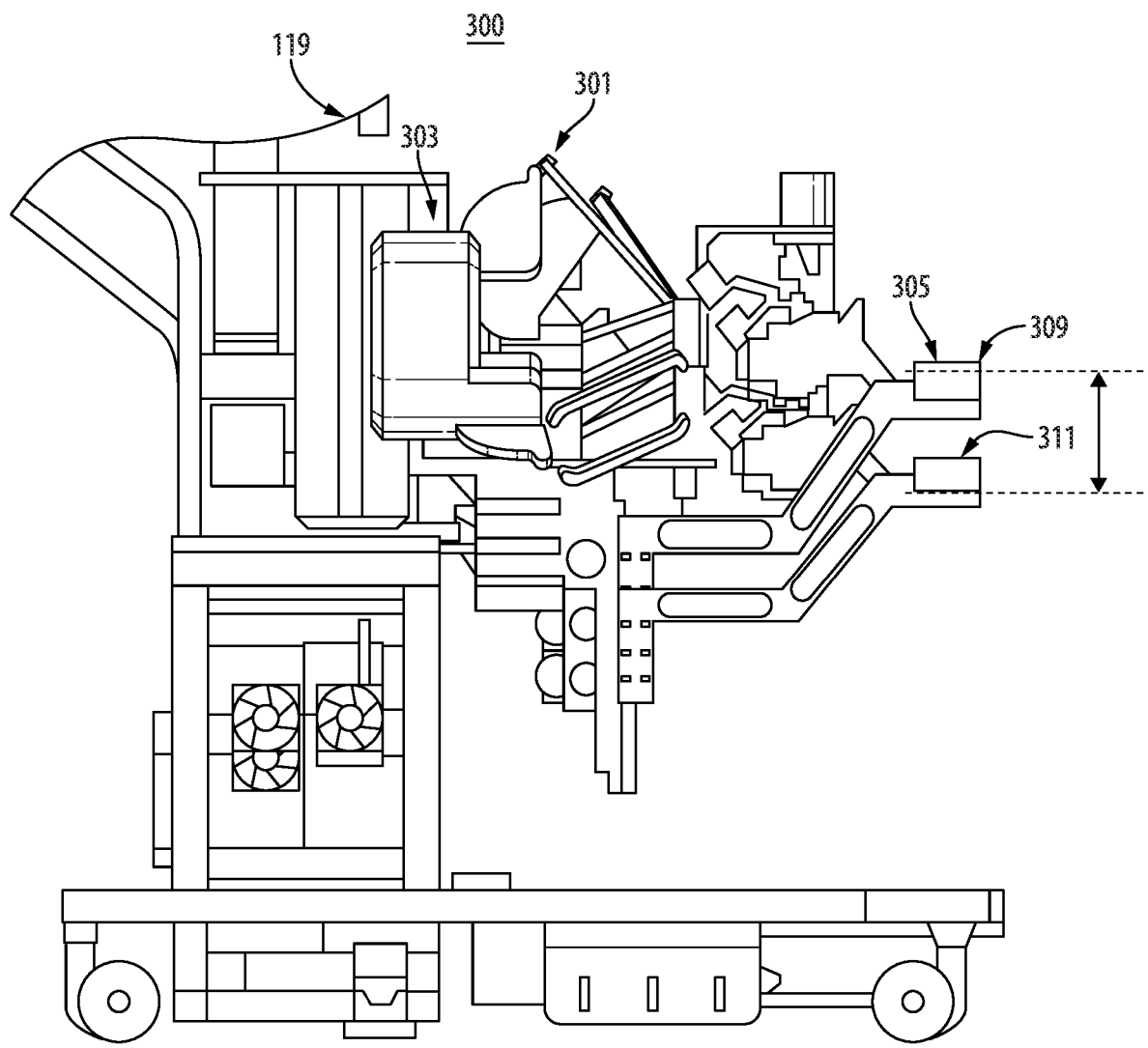
FIG. 5 is an elevation view of the embodiment of FIG. 3, showing vertical arm rest adjustability.
Figure 6:
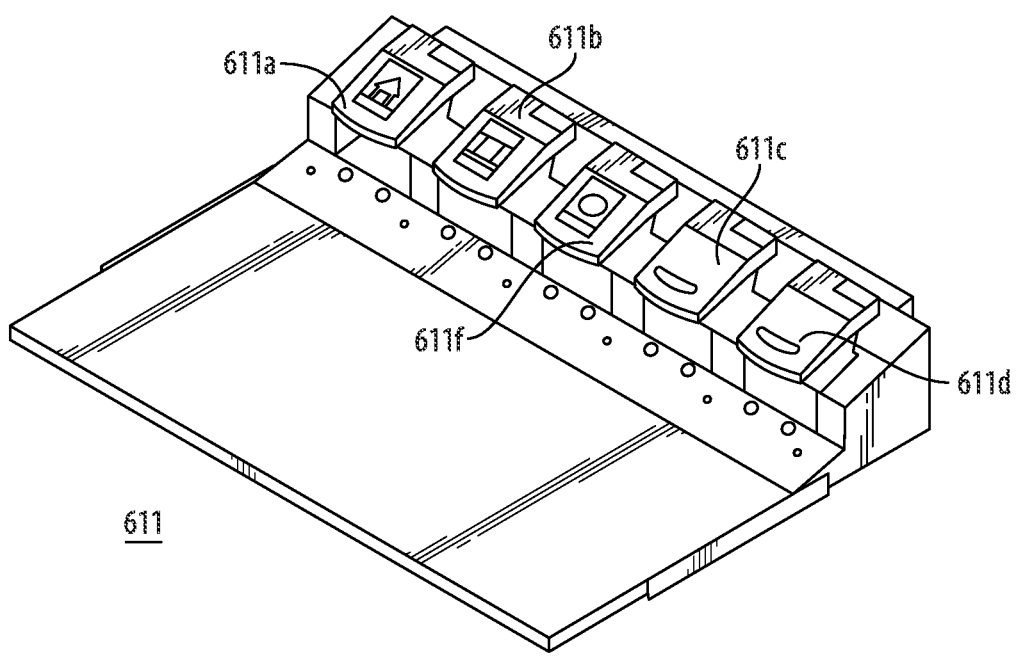
FIG. 6 shows another embodiment of a foot pedal arrangement in accordance with this disclosure.
Figure 8:
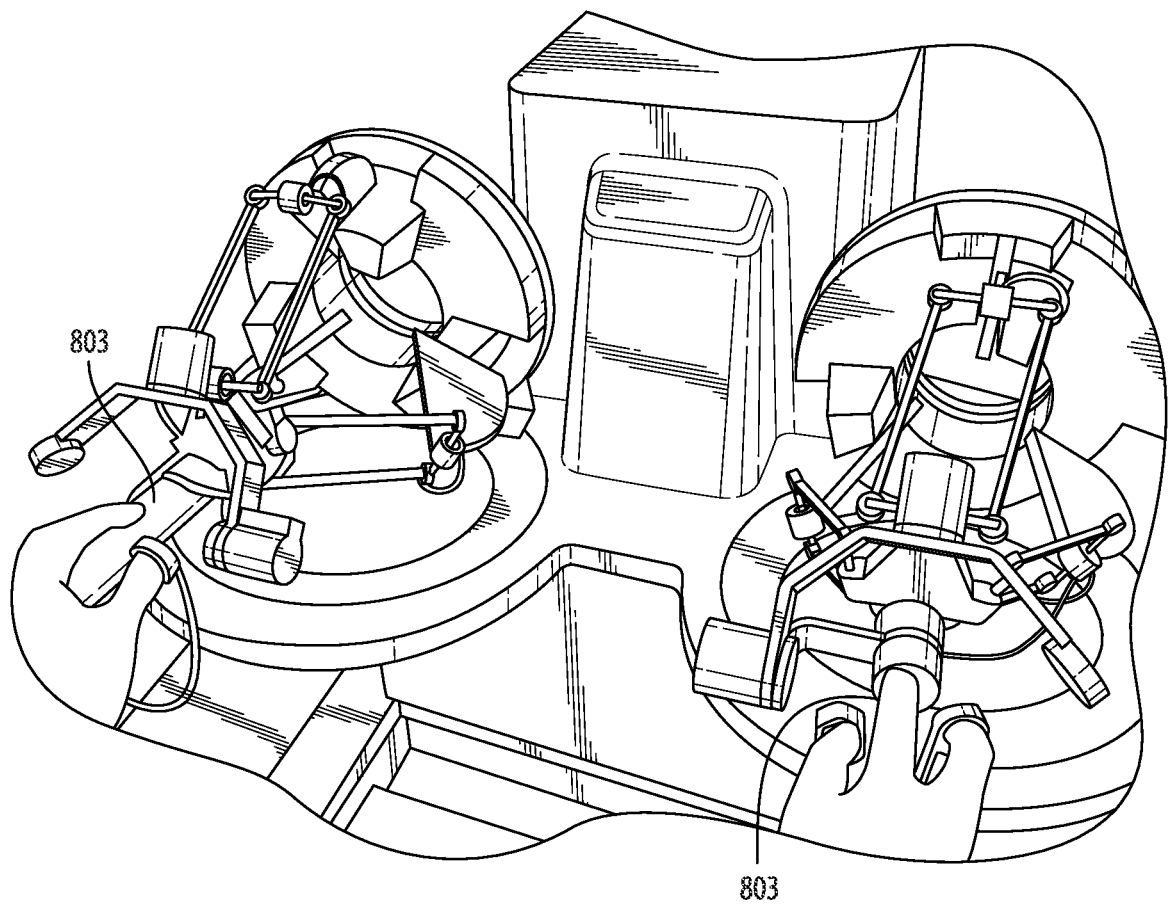
FIG. 8 shows an embodiment of user inputs in accordance with this disclosure on the patient cart.
Figure 9A:
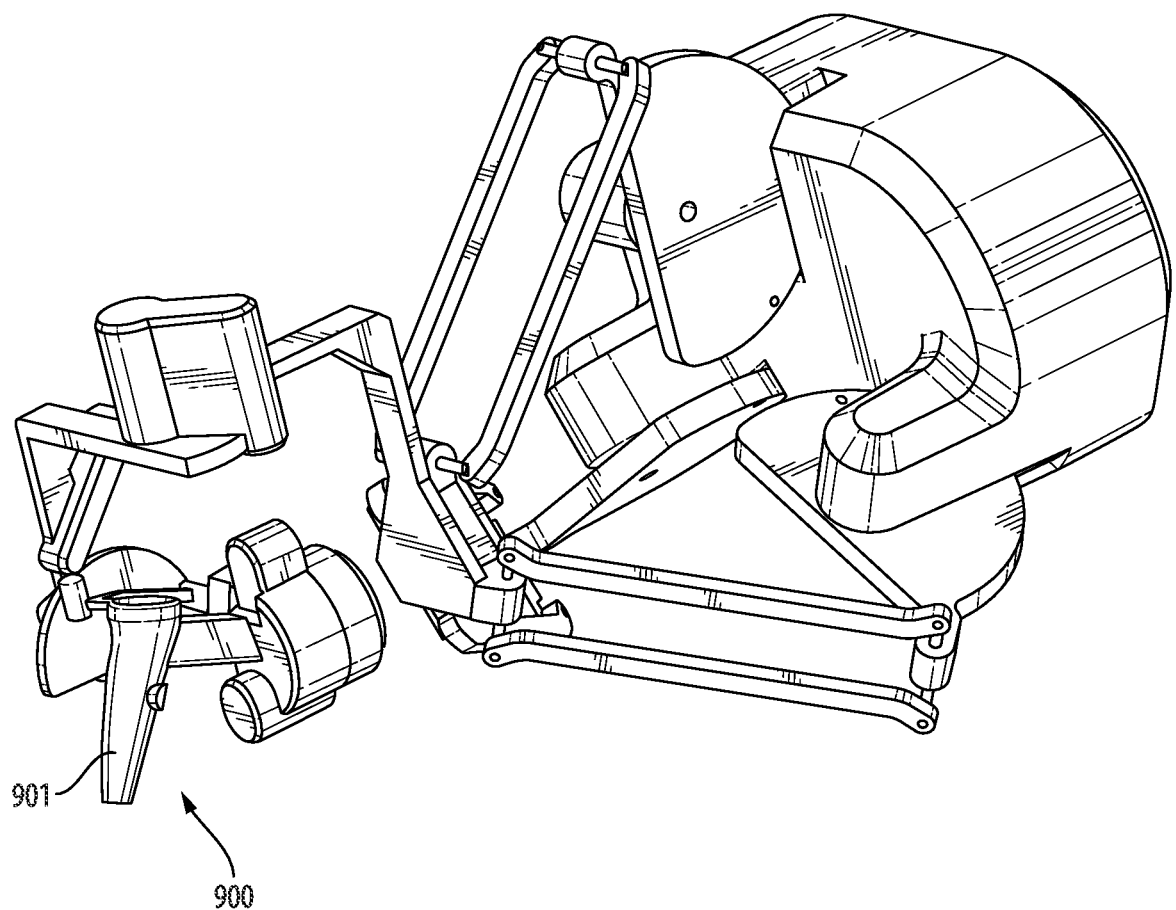
FIG. 9A shows an alternate embodiment of a user input in accordance with this disclosure.
Figure 9B:
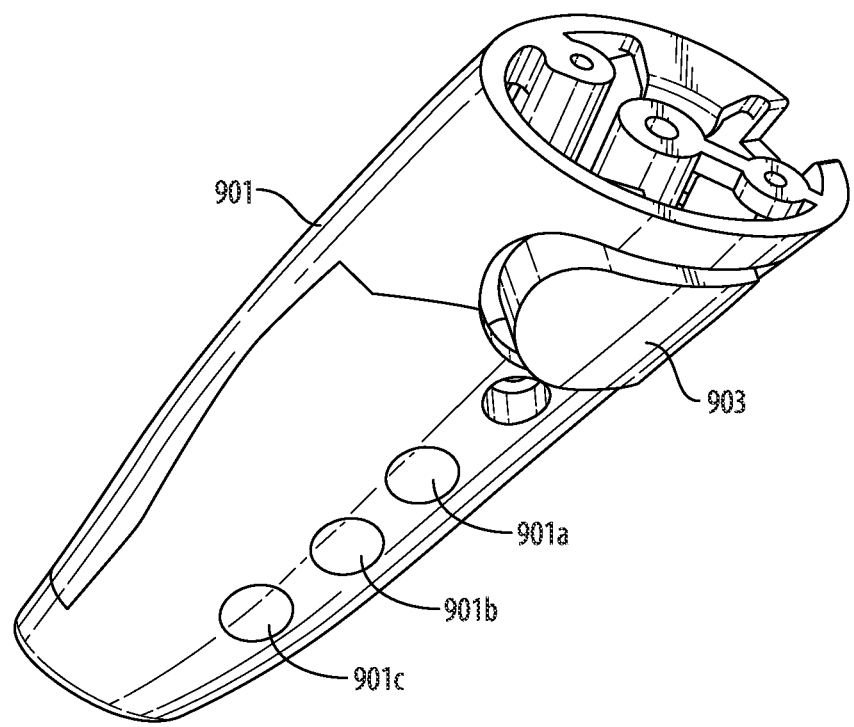
FIG. 9B shows an embodiment of a hand control device of FIG. 9A having a plurality of mode controls thereon in accordance with this disclosure.

FIG. 3 is a perspective view of another embodiment of a user console in accordance with this disclosure. FIG. 4 is an elevation view of the embodiment of FIG. 3, showing horizontal arm rest adjustability. FIG. 5 is an elevation view of the embodiment of FIG. 3, showing vertical arm rest adjustability. FIG. 6 shows another embodiment of a foot pedal arrangement 611 in accordance with this disclosure. FIG. 7 shows a user using inputs on the patient cart, and a display thereof displaying a graphical user interface. FIG. 8 shows an embodiment of user inputs in accordance with this disclosure on the patient cart. FIGS. 9A and 9B show an alternate embodiment of a user input having a pistol grip in accordance with this disclosure.

Embodiments include an overall master control of an endoluminal surgical system (ELS). Embodiments can provide monitoring and positioning of the patient cart 101 and the overtube 106 (also referred to in the Appendices by the trademark Colubriscope™; all rights reserved) by way of the ELS user console.

Embodiments of a user console 107 can include an instrument control that causes an end effector 115 (provided at a distal end of a surgical instrument 116 controlled by the instrument controller 105 as shown in FIG. 7) to move. In certain embodiment, the displayed image 117 on the display 119 of the user console 107 can be changed in response to the movement of the end effector 115. Embodiments of a user console 107 can include a camera control that cause the camera 201 (e.g., mounted to a camera controller 203 above the instrument controller 105 of FIG. 1) to move (e.g., via the same hand controls while the end effector/instrument controllers are locked). The displayed image 117 can be changed in response to the movement of the camera 201. In certain embodiments, the movement of the camera 201 can be controlled by one of the instrument controllers 105 without an additional camera controller. In certain embodiments, the camera controller 203 can be a separate controller (e.g., which can be the same type of controller as the instrument controller(s) for example).

Embodiments can include an overtube control configured to cause the overtube 106 (e.g., which can be a flexible elongated insertion tube having one or more instrument channels therein for the medical device to advance/retract therein) to move while the camera 201 and the end effector 115 mounted thereon are also moved. The displayed image 117 can be changed in response to the movement of the overtube 106, for example.

Control can be made by either a combination of hand control devices (e.g. the hand inputs 109 of FIG. 1) and foot pedals 111, or a combination of hand control devices and a button on the hand control devices, for example. Any suitable control scheme is contemplated herein.

Referring to FIG. 3, for example, the user console 300 can have a dual hand control device 109, 301, 303 (also known as master or hand controller as shown in, e.g., FIG. 3) configuration located across the armrest 305. The relative motion of the hand control devices can be used to control the articulated motion of the surgical instrument 116 A surgeon can hold each of the hand control devices the same way a surgical forceps is held, for example. Embodiments can include a display 119 (e.g., HD image viewer of FIG. 3). The display 119 can provide a 2D view of the surgical workspace captured by the videoscope instrument and displayed to the user as a 2D image on the display 119. The user can also view additional information in the form of text, icons, and graphic content overlaid on the video in the display 119.

Referring to FIG. 3, for example, embodiments can include an armrest 305. The armrest 305 can be adjustable horizontally (e.g., as shown in FIG. 4) or vertically (e.g., as shown in FIG. 5), for example. The armrest panel can be in front of the surgeon to support the arms while the hand control device 301, 303 is held and operated. The armrest 305 can include a left switch panel 309 (left side) and the right switch panel 311 (right side), for example. The left switch panel 309 can provide ergonomic adjustment. The surgeon can make ergonomic adjustments using the controls provided on the left switch panel 309 located on left side of the armrest 305. In certain embodiments, the left switch panel 309 can provide four push buttons to adjust the display 119 and the user console 300, for example. For example, the buttons can include an up button and down button (e.g., a pair in the left). In certain embodiments, a user can press and hold the button of "↑" to increase the elevation of the user console, and release at desired height. In certain embodiments, a user can press and hold the button of "↓" to decrease to decrease the elevation of the user console, and release at a desired height. In certain embodiments, the buttons can include a viewer up button and down button (e.g., a pair in the right). A user can press and hold the button of "↑" to increase the elevation of the display 119, and release at desired height. In certain embodiments, a user can press and hold the button of "↓" to decrease the elevation of the display 119 and release at desired height.

In certain embodiments, the right switch panel 311 can include power control and an emergency stop control. For example, the surgeon (or other operator) can control the system on/off, emergency stop, and EMO recovery functions via controls provided on the right switch panel located on the right side of the arm rest.

The right switch panel 311 can include three buttons, for example (e.g., a power button, an emergency stop button, and an emergency recovery (EMO). For example, a user can press and release a power button to turn the system ON, and can press and hold for 3 seconds to turn the system OFF. For emergency stop, a user can press and release the emergency stop button to stop the operation of the system during an emergency. The user can press and release the EMO recovery button to return the system to the operational state after an emergency stop and when the hazardous situation has been cleared, for example.

While one or more positions for certain buttons are disclosed, any suitable position is contemplated herein. The user console 107 can include any suitable hardware and/or software modules configured to connect to each button, pedal, or other suitable input disclosed herein to perform the disclosed function and/or any other suitable function.

Embodiments of a user console 107 can include one or more foot pedals 111, 611 shown in e.g. FIG. 6 and/or one or more associated control modules configured to enable the below disclosed functions. For example, the surgeon can control various functions by pressing the foot pedals 111 located at the bottom of the user console. In certain embodiments, the surgeon can perform the below described functions by pressing down on various pedals 111.

For example, as shown in FIGS. 2 and 6, the pedals 111, 611 can include a home pedal 111a, 611a that can be pressed and held (e.g., along with the finger clutch button on the hand control device) to bring back the attached instrument to an initial position and/or orientation (e.g., straightened with zero roll and zero pitch, for example). In certain embodiments, the home pedal 111a, 611a may be operational only when the system is not clutched. When clutched, both hand control devices 301, 303 can be decoupled from the instrument controller 105 so that the hand control devices can move freely while instruments remain immobile. For example, in an instrument homing operation, a user can press and hold the home pedal 111a, 611a. Simultaneously, the user can press and hold the finger clutch button on the hand control device to bring the attached surgical instrument 116 back to its straightened pose. A user can move the left hand control devices 301 such that the videoscope flex control indicator shows the straight line both in pitch and yaw indicators.

Embodiments can include a videoscope pedal 111b, 611b. In certain embodiments, a user can press and hold the videoscope pedal 111b, 611b to operate the videoscope using the hand controls, for example. Pressing the videoscope pedal 111b, 611b can disconnect control of the instrument controller(s) 105 and switch it to control of the videoscope (e.g., one or more video scope controllers).

Embodiments can include a cut pedal 111c, 611c. In certain embodiments, a user can press and hold the cut pedal 111c, 611c to use the cut function of an electrosurgical instrument assigned to either the left and/or right hand control device 301, 303. Embodiments can include a coagulation pedal 111d, 611d. In certain embodiments, a user can press and hold the coagulation pedal 111d, 611d to use the coagulate function of the electrosurgical instrument assigned to the left and/or right hand control device 301, 303.

Embodiments can include a clutch pedal 111e. In certain embodiments, a user can press and release the clutch pedal to freeze surgical instrument 116 operations (decoupling the hand control devices 301, 303 from the instrument controllers). For example, in certain embodiments, when the clutch pedal 111e is active, the motion on the hand control device 301, 303 is not relayed to the instrument controllers 105. In certain embodiments, when the clutch pedal 111e is active, the surgeon can operate, for example, the left switch panel 309 to make ergonomic adjustments and reposition the hand control device 301, 303 to attain more workspace. In certain embodiments, the surgeon can retake control of the instruments by pressing and releasing the clutch pedal again.

Embodiments can include an overtube pedal 111f, 611f. The overtube pedal 111f, 611f can be used to adjust the location of the instrument workspace, for example. In certain embodiments, a user can press and hold the overtube pedal 111f, 611f to operate the positioning system of the patient cart 101 using the left-hand control device 301 (or right hand control device 303) to control translation and roll motions of the overtube 106. In certain embodiments, a user can press and hold to operate the overtube 106 using the other side hand control (e.g., right hand) device to control the flexible motion of the overtube 106.

In certain embodiments, a user can press and hold the overtube pedal 111f, 611f and then use the left and right hand control device 301, 303 to alter the workspace and view. In certain embodiments, the left hand device 301 can control insertion/retraction and roll motions. In certain embodiments, the right hand device 303 can control pitching and yawing motions. In certain embodiments, during the operation of the overtube pedal 111f, 611f, all surgical instruments holds their positions (e.g., the instrument controllers 105 lock to cause the instruments to remain immobile).

Embodiments can include a suction pedal 111g. For example, when a suction device is connected to the overtube, the user can press and hold the suction pedal 111g for suction. Embodiments can include an insufflation pedal 111h. For example, when an insufflator is connected to the overtube 106, the user can press and hold insufflation pedal 111h for insufflation adjustment.

Embodiments can include an emergency stop button (not shown) on the right switch panel 311. For example, the emergency stop button can be used to freeze all operations related to the patient cart in case of an emergency. All movement can stop and an instrument controller 105 motor brake can be released and can be retracted manually. In an emergency state, the instrument controller 105 can move freely. The instrument controller 105 can further include an instrument clutch button (not shown) on its housing, which can flash in red in the emergency state. In an emergency state, all the cable tensions can be loosened, and the surgical instrument 116 will not have any grasping force nor segment bending force. In certain embodiments, the system can ensure the instrument 116 is grasping a tissue or a suture needle in the working space.

Embodiments can include a finger clutch button 803, 903 (e.g., as shown in FIGS. 8 and 9B) for example. In certain embodiments, a user can press and hold the finger clutch button 803, 903 to hold the position and pose of the surgical instrument 116 connected to the respective hand control device 301, 303 (regardless of the motion of that hand control device). In certain embodiments, the motion of the hand control device 301, 303 will not be relayed to the respective surgical instruments 116 when the finger clutch button 803, 903 is pressed and held. The user can use the finger clutch button 803, 903 to reposition the hand control device 301, 303 without changing the instrument 116 pose for easy maneuvering of the workspace.

In accordance with at least one aspect of this disclosure, referring to FIGS. 1, 1A, 9A, and 9B, for example, a robotic surgical system can include any suitable robotic surgical system as disclosed herein, e.g., system 100 as described above. In certain embodiments, however, the system 100 can include one or more hand control devices 900 (e.g., having a pistol grip 901) having a plurality of mode selection controls 901a, 901b, 901c thereon configured to output one or more input control mode signals (e.g., one or more hand control mode signals). The hand control device 900 can be configured to receive user inputs and output position control signals (e.g., for controlling one or more instruments).

The system can include a control module (e.g., 114 of FIG. 1B as described above) operatively connected to the one or more instrument controllers (e.g., 105 as described above), the camera controller (e.g., 203 as described above), and the overtube controller (e.g., 108 as described above), and can be configured to receive the one or more input control mode signals from the one or more hand control devices 900. The control module (e.g., 114 as described above) can be configured to select between a plurality of modes as a function of the one or more input control mode signals. For example, the modes can include an instrument control mode (e.g., activated by actuating mode control 901a) wherein the control module 114 is configured cause the end effector to move by controlling the one or more robotic instrument controllers 105 as a function of the position control signals. The modes can include a camera control mode (e.g., activated by actuating mode control 901b) wherein the control module is configured to cause the camera 201 to move by controlling the robotic camera controller 203 as a function of the position control signals. The modes can include an overtube control mode (e.g., activate by actuating mode control 901c) wherein the control module is configured to cause the overtube 106 to move by controlling the robotic overtube controller 108, while the camera and the end effector mounted therewith are also moved by virtue of the motion of the overtube, as a function of the position control signals.

In certain embodiments, as shown in FIGS. 9A and 9B, the one or more hand control devices 900 can include a pistol grip 901, for example. In certain embodiments, the one or more mode selection controls 901a, b, c can include a mode selection button for each mode (e.g., three buttons as shown). The placement of the mode selection controls 901a, b, c can be ergonomically selected. For example, the controls 901a, b, c can be mounted where a user's fingers will wrap around the pistol grip 901, providing a location at or easily reachable from the location of the fingertips of the user. In certain embodiments, the pistol grip 901 can include a clutch button 903 positioned on the same side as the controls 901a, b, c and configured to be actuated by a user's thumb or index finger, for example.

Any suitable button or actuation type for the controls 901a, 901b, 901c are contemplated herein. For example, the resistance of the controls 901a, 901b, 901c can be selected to be sufficiently high to avoid accidental actuation. Each mode control 901a, 901b, 901c may have a different button or actuation type so that a user does not confuse the various mode controls. For example, the control 901a can be a push button, the control 901b can be a rocker switch, and the control 901c can be a sliding switch. Any other suitable arrangement of different types, sizes, and/or shapes of controls is contemplated herein. Such embodiments having hand device mode controls can allow a user to switch between states without foot pedals and in a seamless intuitive fashion, reducing operation times.

In accordance with at least one aspect of this disclosure, a control module (e.g., module 114) for a robotic surgical system (e.g., system 100 as described above) can be configured to receive one or more user inputs and to select between a plurality of modes as a function of the one or more user inputs, e.g., as described above. In addition to the any combination of modes as described above, the modes can also include a 2-dimensional (2D) imaging mode configured to output a 2-dimensional image from the camera, and a 3-dimensional (3D) imaging mode configured to output a 3-dimensional image from the camera. In some examples, the 2D imaging mode and 3D imaging mode are selectable to be functioned alone or with one another. In other examples, the modes can further include a switch mode configured to convert one of these two imaging modes to one another. Any other additional suitable image processing, converting and/or image selection modes, processors and/or converters are contemplated herein. Any suitable location for one or more mode control locations for the 2D and 3D mode is contemplated herein.

In certain embodiments, the robotic surgical system further comprises one or more instrument controllers (e.g., as described above) configured to move and position a respective instrument having a respective end effector, a robotic camera controller configured to move and position a camera, a robotic overtube controller configured to move and position an overtube and one or more hand control devices having a plurality of mode selection controls thereon configured to output one or more input control mode signals, and configured to receive user inputs and output position control signals. In certain embodiments, the control module is in communication with the one or more instrument controllers, the robotic camera controller, or the robotic overtube controller to operate the one or more instrument controllers, the robotic camera controller, or the robotic overtube controller as a function of the one or more input control mode signals.

Certain embodiments can be used for trans-anal procedures, trans-vaginal procedures, and/or trans-esophageal procedures, for example. Certain embodiments can be used for transluminal procedures in any suitable body lumen. Certain embodiments can be used in single incision procedures, for example. Certain embodiments can be used for any suitable procedure.

Figure 12A:
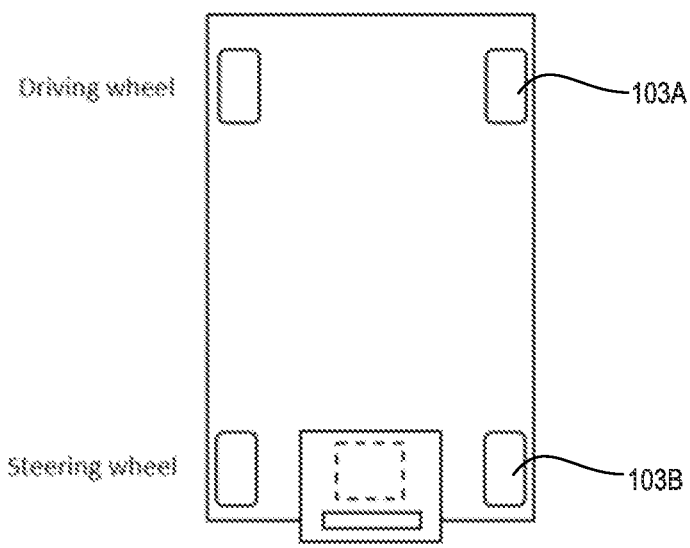
FIG. 12A shows an embodiment of front wheels and rear wheels of a patient cart in an unmoved state in accordance with this disclosure.
Figure 12B:
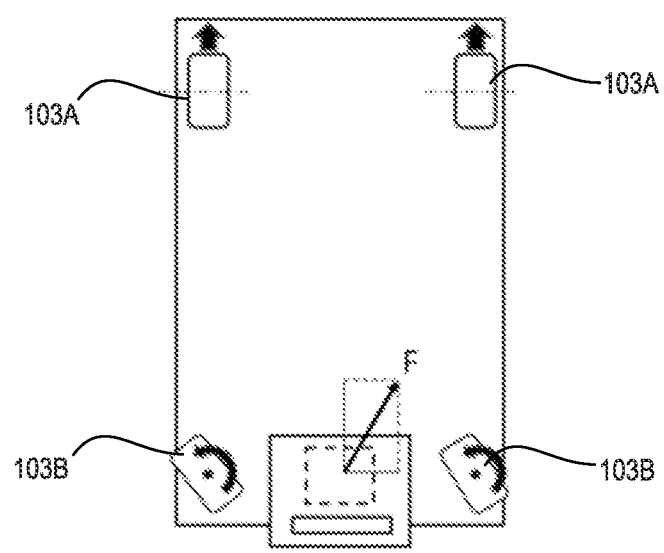
FIG. 12B shows an embodiment of front wheels and rear wheels of FIG. 12A in moving state in accordance with this disclosure.

In certain embodiments, as shown in FIGS. 12A and 12B, the mobile base 103 of the patient cart 101 can further include a pair of front wheels 103A and a pair of rear wheels 103B.

The front wheels 103A can function as driving wheels which are allowed to move back and forth relative to a floor. The rear wheels 103B, on the other hand, can function as steering wheels (for example, swivel casters) which are allowed to freely rotate about its rotating axis, thus enabling the wheels 103B to roll in any direction as shown in FIG. 12B. In certain embodiments, each front wheels 103A and rear wheels 103B can further include a dedicated locking mechanism (not shown) to lock the wheels 103A and 103B into a fixed position.

In certain embodiments, the patient cart motion control module 113 can be configured to select between a plurality of wheel control modes for wheels 103A and 103B as a function of the one or more user inputs. For example, when applying force F by pushing or pulling on the patient cart handle 1102 in a lateral direction while partially depressing the one or more grip actuators 1101, the patient cart 101 can be steered through the back and forth movements of the front wheels 103A and the rotation of the rear wheels 103B. For example, any force F having a lateral component can cause the rear wheels 103B to rotate (e.g., by operation of a motor) in a direction that results in turning of the base in the direction of lateral component (e.g., as shown, counterclockwise for a right turn and clockwise for a left turn). In certain embodiments, applying force can include pushing or pulling on the patient cart handle in a lateral direction while partially depressing the one or more grip actuators to steer the patient cart.

As will be appreciated by those skilled in the art, aspects of the present disclosure may be embodied as a system, method or computer program product. Accordingly, aspects of this disclosure may take the form of an entirely hardware embodiment, an entirely software embodiment (including firmware, resident software, micro-code, etc.), or an embodiment combining software and hardware aspects, all possibilities of which can be referred to herein as a "circuit," "module," or "system." A "circuit," "module," or "system"

can include one or more portions of one or more separate physical hardware and/or software components that can together perform the disclosed function of the "circuit," "module," or "system", or a "circuit," "module," or "system" can be a single self-contained unit (e.g., of hardware and/or software). Furthermore, aspects of this disclosure may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of this disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of this disclosure may be described above with reference to flowchart illustrations and/or block diagrams of methods, apparatus (systems) and computer program products according to embodiments of this disclosure. It will be understood that each block of any flowchart illustrations and/or block diagrams, and combinations of blocks in any flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in any flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Those having ordinary skill in the art understand that any numerical values disclosed herein can be exact values or can be values within a range. Further, any terms of approximation (e.g., "about", "approximately", "around") used in this disclosure can mean the stated value within a range. For example, in certain embodiments, the range can be within (plus or minus) 20%, or within 10%, or within 5%, or within 2%, or within any other suitable percentage or number as appreciated by those having ordinary skill in the art (e.g., for known tolerance limits or error ranges).

The articles "a", "an", and "the" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

Any suitable combination(s) of any disclosed embodiments and/or any suitable portion(s) thereof are contemplated herein as appreciated by those having ordinary skill in the art in view of this disclosure.

The embodiments of the present disclosure, as described above and shown in the drawings, provide for improvement in the art to which they pertain. While the subject disclosure includes reference to certain embodiments, those skilled in the art will readily appreciate that changes and/or modifications may be made thereto without departing from the spirit and scope of the subject disclosure.

What is claimed is:

1. A robotic surgical system, comprising:
   one or more robotic instrument controllers configured to move and position a respective instrument having a respective end effector;
   a robotic camera controller configured to move and position a camera;
   a robotic overtube controller configured to move and position an overtube, wherein the one or more instruments extend through the overtube such that the end effectors extend from a distal end of the overtube, wherein the camera extends through the overtube and extends from the distal end of the overtube;
   one or more input control devices having a plurality of mode selection controls thereon configured to output one or more input control mode signals, and configured to receive user inputs and output position control signals;
   a control module operatively connected to the one or more instrument controllers, the camera controller, and the overtube controller, wherein the control module is configured to:
   receive the one or more input control mode signals from the one or more input control devices, and to select between a plurality of modes as a function of the one or more input control mode signals, wherein the modes include:
   an instrument control mode wherein the control module is configured cause the end effector to move by controlling the one or more robotic instrument controllers as a function of the position control signals;
   a camera control mode wherein the control module is configured to cause the camera to move by controlling the robotic camera controller as a function of the position control signals; and
   an overtube control mode wherein the control module is configured to cause the overtube to move by controlling the robotic overtube controller, while the camera and the end effector mounted therewith are also moved by virtue of the motion of the overtube, as a function of the position control signals.

2. The system of claim 1, wherein the one or more input control devices include a hand control device having a pistol grip, wherein the one or more mode selection controls include a mode selection button for each mode.

3. The system of claim 1, wherein the one or more input control devices further include one or more foot pedals which is configured to output a plurality of mode selection controls.

4. A control module for a robotic surgical system, configured to:
   receive one or more user inputs and to select between a plurality of modes as a function of the one or more user inputs, wherein the modes include:
   an instrument control mode wherein the control module is configured cause an end effector to move by controlling one or more robotic instrument controllers as a function of the position control signals;
   a camera control mode wherein the control module is configured to cause a camera to move by controlling a robotic camera controller as a function of the position control signals; and
   an overtube control mode wherein the control module is configured to cause the overtube to move by controlling a robotic overtube controller, while the camera and the end effector mounted therewith are also moved by virtue of the motion of the overtube, as a function of the position control signals.

5. The control module of claim 4, further comprising:
   a 2-dimensional imaging mode configured to output a 2-dimensional image from the camera; and
   a 3-dimensional imaging mode configured to output a 3-dimensional image from the camera.

6. The control module of claim 4, wherein the robotic surgical system further comprises one or more instrument controllers configured to move and position a respective instrument having a respective end effector, a robotic camera controller configured to move and position a camera, a robotic overtube controller configured to move and position an overtube and one or more input control device having a plurality of mode selection controls thereon configured to output one or more input control mode signals, and configured to receive user inputs and output position control signals.

7. The control module of claim 6, wherein the control module is in communication with the one or more instrument controllers, the robotic camera controller, or the robotic overtube controller through the one or more input control mode signals.

* * * * *